United States Patent
Kawde et al.

(10) Patent No.: US 10,031,103 B2
(45) Date of Patent: Jul. 24, 2018

(54) METHOD FOR DETERMINING PHENOL CONCENTRATION BY USING GRAPHITE PENCIL ELECTRODE SYSTEM

(71) Applicant: KING FAHD UNIVERSITY OF PETROLEUM AND MINERALS, Dhahran (SA)

(72) Inventors: Abdel-Nasser M. Kawde, Dhahran (SA); Azeem A. Rana, Dhahran (SA)

(73) Assignee: King Fahd University of Petroleum and Minerals, Dhahran (SA)

(*) Notice: Subject to any disclaimer, the term of this patent is extended or adjusted under 35 U.S.C. 154(b) by 214 days.

(21) Appl. No.: 15/069,450

(22) Filed: Mar. 14, 2016

(65) Prior Publication Data
US 2017/0261467 A1    Sep. 14, 2017

(51) Int. Cl.
*G01N 27/42* (2006.01)
*G01N 27/30* (2006.01)
*G01N 33/18* (2006.01)

(52) U.S. Cl.
CPC ........... *G01N 27/42* (2013.01); *G01N 27/308* (2013.01); *G01N 33/1826* (2013.01)

(58) Field of Classification Search
CPC ...... G01N 27/42; G01N 27/44; G01N 27/308; G01N 33/1826
See application file for complete search history.

(56) References Cited

FOREIGN PATENT DOCUMENTS

| CN | 102249377 B | 10/2012 |
|----|-------------|---------|
| CN | 102928488 B | 9/2014  |

OTHER PUBLICATIONS

Mengoli et al., "An Overview of Phenol Electropolymerization for Metal Protection," Journal of the Electrochemical Society—Reviews and News, pp. 643C-65C, Dec. 1967 (Year: 1967).*

Vieira et al, Electrochemical Modification of Graphite Electrodes with Poly(4-aminophenol), Macromol. Symp. 2006, 245-246, pp. 236-242.*

(Continued)

*Primary Examiner* — Alexander Stephan Noguerola
(74) *Attorney, Agent, or Firm* — Oblon, McClelland, Maier & Neustadt, L.L.P.

(57) ABSTRACT

A method of determining a concentration of phenol and/or a phenol derivative in a first solution. The method includes (a) subjecting a graphite pencil electrode system comprising a graphite pencil working electrode, a counter electrode, and a reference electrode to cyclic voltammetry in a second solution such that a surface of the graphite pencil working electrode is charged by the cyclic voltammetry to form a charged surface, (b) contacting the charged surface of the graphite pencil working electrode with the first solution for sufficient time to electropolymerize the phenol and/or the phenol derivative on the charged surface in open circuit fashion, and (c) determining the concentration of the phenol and/or the phenol derivative in the first solution, wherein the amount of the electropolymerized phenol and/or the electropolymerized phenol derivative formed on the charged surface correlates with the concentration of the phenol and/or the phenol derivative in the first solution.

20 Claims, 18 Drawing Sheets

(56) References Cited

OTHER PUBLICATIONS

Hou et al., "Electropolymerization of Sulfonated Phenol by Cyclic Voltammetry," Journal of Applied Polymer Science 2013, 1151-1156.*

Franco et al., "Electropolymerization of 3-aminophenol on carbon graphite surface: Electric and morphologic properties," Materials Chemistry and Physics 107 (2008) 404-409.*

David et al., "Disposable carbon electrodes as an alternative for the direct voltammetric determination of alkyl phenols from water samples," Turkish Journal of Chemistry (2013) 37 : 91-100.*

K. F. Blurton, "An Electrochemical Investigation of Graphite Surfaces," Electrochimica Acta, 1973, vol. 18, pp. 869-785.*

El Mhammedi et al., Electrochemical determination of para-nitrophenol at apatite-modified carbon paste electrode: Application in river water samples, Journal of Hazardous Materials 163 (2009) 323-328 (Year: 2008).*

Belkamssa et al., "Electrochemical detection of phenolic estrogenic compounds at clay modified paste electrode," Tunisia-Japan Symposium: R & D of Energy and Material Sciences, Journal of Physics Conference Series 596 (2015) 012014 (Year: 2015).*

Hourdin et al., "Thermally Induced Transient Activity Changes of Plasmin Adsorbed onto Bare and Fibrinogen-Modified Graphite and Glassy Carbon Surfaces," Journal of Colloid and Interface Science 236, 132-140 (Year: 2001).*

Vu et al., "Sensitive Voltammetric Determination of Natural Flavonoid Quercetin on a Disposable Graphite Lead," Food Technol. Biotechnol. 53(4) 379-384 (2015) (Year: 2015).*

Vu et al., "Voltammetric Determination of Tannic Acid in Beverages using Pencil Graphite Electrode," Food Analysis, Food Quality and Nutrition, Czech J. Food Sci., 33, 2015 (1): 72-67 (Year: 2015).*

I.David et al., "Disposable carbon electrodes as an alternative for the direct voltammetric determination of alkyl phenols from water samples" Turkish Journal of Chemistry, Jan. 2013, pp. 91-100.

D. Franco et al., "Electropolymerization of 3-aminophenol on carbon graphite surface: Electric and morphologic properties", Materials Chemistry and Physics, vol. 107, Issue 2-3, Feb. 2008, pp. 404-409.

F. Ortega et al., "Amperometric biosensor for the determination of phenolic compounds using a tyrosinase graphite electrode in a flow injection system" Journal of Biotechnology,vol. 31, Dec. 1993, pp. 289-300.

A. Rana et al., "Open-Circuit Electrochemical Polymerization for the Sensitive Detection of Phenols" Electroanalysis, 2015, pp. 1-9.

* cited by examiner

METHOD FOR DETERMINING PHENOL CONCENTRATION BY USING GRAPHITE PENCIL ELECTRODE SYSTEM

BACKGROUND OF THE INVENTION

Technical Field

The present disclosure relates to detection methods of phenol and its derivatives. More specifically, the present disclosure relates to a method of determining a concentration of phenol and/or a phenol derivative in a solution with a graphite pencil electrode system, wherein a surface of the graphite pencil working electrode is charged by voltammetry and the phenol and/or its derivative to be detected are subsequently electropolymerized on the charged surface of the graphite pencil working electrode in open circuit fashion and quantified by voltammetry.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, is neither expressly nor impliedly admitted as prior art against the present invention.

Phenol and its derivatives are common pollutants produced by various industries, such as petroleum, paper, plastic, pharmaceutical, and pesticide manufacturing. These pullutants may be found in water samples from river water, lake water, ground water, waste water, a refinery industry effluent, a chemical industry effluent, a paper industry effluent, etc.

Phenol and its derivatives are toxic. Phenol and its vapors are corrosive to the eyes, the skin, and the respiratory tract. Its corrosive effect on the skin and mucous membranes is due to a protein-degenerating effect. Repeated or prolonged skin contact with phenol or its derivatives may cause dermatitis, or even second and third-degree burns. Exposure to phenol and its derivatives may also result in damages to the central nervous system and the heart, leading to dysrhythmia, seizures, and coma. Additionally, long-term or repeated exposure to phenol and its derivatives may have harmful effects on the liver and kidneys. Thus, it is critical to monitor the levels of phenol and its derivatives in the environment, particularly in the water systems.

Various analytical techniques have been developed for phenol detection. These techniques include spectrophotometry, chromatography, and electroanalytical methods (See S. Amlathe, V. K. Gupta, Spectrophotometric determination of phenol in air, Fresenius. J. Anal. Chem. 339 (1991) 199-200; W. Medjor, C. Wepuaka, S. Godwill, Spectrophotometric Determination of Phenol in Natural Waters by Trichloromethane Extraction Method after Steam Distillation, Int. Res. J. Pure Appl. Chem. 7 (2015) 150-156; S. Chakravarty, M. K. Deb, R. K. Mishra, Simple Spectrophotometric Determination of Phenol in Industrial Waste Water, Asian J. Chem. 6 (1994) 766-770; J.-J. Ye, W. Feng, M.-M. Tian, J.-L. Zhang, W.-H. Zhou, Q. Jia, Spectrophotometric determination of phenol by flow injection on-line preconcentration with a micro-column containing magnetic microspheres functionalized with Cyanex272, Anal. Methods. 5 (2013) 1046; O. Agrawal, V. K. Gupta, Sub-Parts-per-Million Spectrophotometric Determination of Phenol and Related Pesticides Using Diazotizedp-Aminoacetophenone, Microchem. J. 62 (1999) 147-153; J. P. Rawat, K. P. Singh Muktawat, Sensitive, selective spectrophotometric determination of phenols with periodic acid, Microchem. J. 30 (1984) 289-296; Y. Fiamegos, C. Stalikas, G. Pilidis, M. Karayannis, Synthesis and analytical applications of 4-aminopyrazolone derivatives as chromogenic agents for the spectrophotometric determination of phenols, Anal. Chim. Acta. 403 (2000) 315-323; M. Nassiri, M. M. Zahedi, S. M. Pourmortazavi, M. Yousefzade, Optimization of dispersive liquid-liquid microextraction for preconcentration and spectrophotometric determination of phenols in Chabahar Bay seawater after derivatization with 4-aminoantipyrine., Mar. Pollut. Bull. 86 (2014) 512-7; R. Sun, Y. Wang, Y. Ni, S. Kokot, Spectrophotometric analysis of phenols, which involves a hemingraphene hybrid nanoparticles with peroxidase-like activity., J. Hazard. Mater. 266 (2014) 60-7; N. Venugopal, A. Vijaya Bhaskar Reddy, G. Madhavi, Development and validation of a systematic UPLC-MS/MS method for simultaneous determination of three phenol impurities in ritonavir., J. Pharm. Biomed. Anal. 90 (2014) 127-33; I. V. Gruzdev, I. M. Kuzivanov, I. G. Zenkevich, B. M. Kondratenok, Gaschromatographic identification of products formed in iodination of methyl phenols by retention indices, Russ. J. Appl. Chem. 85 (2012) 1355-1365; M. T. Oliva-Teles, C. Delerue-Matos, H. P. a. Nouws, M. C. M. Alvim-Ferraz, Chromatographic Techniques for the Determination of Free Phenol in Foundry Resins, Anal. Lett. 44 (2011) 1536-1543; H. Gao, W. Cao, Y. Liang, N. Cheng, B. Wang, J. Zheng, Determination of Thymol and Phenol in Honey by LC with Electrochemical Detection, Chromatographia. 72 (2010) 361-363; R. Sadeghi, H. Karimi-Maleh, M. A. Khalilzadeh, H. Beitollahi, Z. Ranjbarha, M. B. P. Zanousi, A new strategy for determination of hydroxylamine and phenol in water and waste water samples using modified nanosensor., Environ. Sci. Pollut. Res. Int. 20 (2013) 6584-93; H. Guan, X. Liu, W. Wang, Encapsulation of tyrosinase within liposome bioreactors for developing an amperometric phenolic compounds biosensor, J. Solid State Electrochem. 17 (2013) 2887-2893; J. Ren, T.-F. Kang, R. Xue, C.-N. Ge, S.-Y. Cheng, Biosensor based on a glassy carbon electrode modified with tyrosinase immmobilized on multiwalled carbon nanotubes, Microchim. Acta. 174 (2011) 303-309; and N. Negash, H. Alemu, M. Tessema, Determination of Phenol and Chlorophenols at Single-Wall Carbon Nanotubes/Poly (3,4-ethylenedioxythiophene) Modified Glassy Carbon Electrode Using Flow Injection Amperometry, Am. J. Anal. Chem. 5 (2014) 188-198, each incorporated herein by reference in their entirety).

However, most of these methods are time consuming and costly, because they require pretreatment, extraction, and surface assimilation (See Z. Zhong, G. Li, R. Wu, B. Zhu, Z. Luo, Determination of aminophenols and phenol in hair colorants by ultrasound-assisted solid-phase dispersion extraction coupled with ion chromatography, J. Sep. Sci. 37 (2014) 2208-2214; and N. N. M. Zain, N. K. Abu Bakar, S. Mohamad, N. M. Saleh, Optimization of a greener method for removal phenol species by cloud point extraction and spectrophotometry, Spectrochim. Acta—Part A Mol. Biomol. Spectrosc. 118 (2014) 1121-1128, each incorporated herein by reference in their entirety). Electrochemical methods have attracted the attention for the detection of phenol due to their low cost, simplicity, and speed, however, the continuous formation of an adhesive and semipermeable layer comprising the electrooxidation products of phenol on the surface of solid electrodes has made the electrochemical detection of phenol challenging (See X. Yang, J. Kirsch, J. Fergus, A. Simonian, Modeling analysis of electrode fouling during electrolysis of phenolic compounds, Electrochim. Acta. 94 (2013) 259-268, incorporated herein by reference in its entirety).

It is thus an object of the present disclosure to provide an electrochemical method of determining a concentration of phenol and/or a phenol derivative in a solution using a graphite pencil electrode system, wherein a surface of the graphite pencil working electrode is charged by voltammetry and the phenol and/or its derivative to be detected are subsequently electropolymerized on the charged surface of the graphite pencil working electrode in open circuit fashion and quantified by voltammetry, preferably square wave voltammetry. The disclosed method advantageously overcomes the fouling of an electrode surface by phenol while exhibiting a high sensitivity, a satisfactory linear range, and a low detection limit of phenol.

BRIEF SUMMARY OF THE INVENTION

The present disclosure relates to a method of determining a concentration of phenol and/or a phenol derivative in a first solution containing the phenol and/or the phenol derivative. The method includes (a) subjecting a graphite pencil electrode system to cyclic voltammetry in a second solution, wherein the graphite pencil electrode system comprises a graphite pencil working electrode, a counter electrode, and a reference electrode, and wherein a surface of the graphite pencil working electrode is charged by the cyclic voltammetry to form a charged surface, (b) contacting the charged surface of the graphite pencil working electrode with the first solution for a sufficient period of time to electropolymerize the phenol and/or the phenol derivative on the charged surface of the graphite pencil working electrode in open circuit fashion, and (c) determining the concentration of the phenol and/or the phenol derivative in the first solution, wherein the amount of the electropolymerized phenol and/or the electropolymerized phenol derivative formed on the charged surface of the graphite pencil working electrode correlates with the concentration of the phenol and/or the phenol derivative in the first solution.

In one or more embodiments, the first solution has a pH of about 3-14.

In one or more embodiments, the second solution comprises at least one phosphate dibasic salt or at least one metal hydroxide.

In one or more embodiments, the cyclic voltammetry has a potential range of 0.6-4 V.

In one or more embodiments, the cyclic voltammetry has 20-80 voltammetric cycles.

In one or more embodiments, the cyclic voltammetry has a scan rate of 50-200 mV/s.

In one or more embodiments, the sufficient period of time in (b) is about 50-150 seconds.

In one or more embodiments, the phenol derivative is at least one selected from the group consisting of an alkylphenol, a catechol, a trihydroxybenzene, a bisphenol, and a hydroxybiphenyl.

In one or more embodiments, a time interval between the end of the subjecting in (a) and the start of the contacting in (b) is no greater than 15 minutes.

In one or more embodiments, no greater than 25% of the electropolymerized phenol formed on the charged surface of the graphite pencil working electrode is lost at least 5 hours after the end of the contacting in (b).

In one or more embodiments, the determining the concentration of the phenol and/or the phenol derivative in the first solution comprises subjecting the graphite pencil working electrode having the electropolymerized phenol and/or the electropolymerized phenol derivative formed on the charged surface, the counter electrode, and the reference electrode to square wave voltammetry in a third solution to determine the concentration of the phenol and/or the phenol derivative in the first solution based on the amount of the electropolymerized phenol and/or the electropolymerized phenol derivative formed on the charged surface of the graphite pencil working electrode. The square wave voltammetry comprises: (a) applying a pulsed potential to the graphite pencil working electrode while sweeping the potential of the graphite pencil working electrode from a potential that is less than an oxidation peak potential of the electropolymerized phenol and/or the electropolymerized phenol derivative in the third solution positively to a potential that is at least the oxidation peak potential of the electropolymerized phenol and/or the electropolymerized phenol derivative in the third solution, and (b) recording the amount of a forward pulse current and a reverse pulse current during each square wave cycle.

In one or more embodiments, the third solution has a pH of 2-10.

In one or more embodiments, the oxidation peak potential of the electropolymerized phenol in the third solution ranges from about 0.0 V to about 1.0 V.

In one or more embodiments, the amplitude of the pulsed potential is about 0.02-0.10 V.

In one or more embodiments, the voltage step of the square wave voltammetry is about 3-5 mV.

In one or more embodiments, the frequency of the pulsed potential is about 10-100 Hz.

In one or more embodiments, the first solution has a lowest phenol concentration of about 3-60 nM.

In one or more embodiments, the square wave voltammetry further comprises plotting the difference in current between the forward pulse current and the reverse pulse current during each square wave cycle, the difference in current represented by i, against the applied potential of the graphite pencil working electrode to obtain a square wave voltammogram, and measuring the magnitudes of peak changes in i in the square wave voltammogram.

In one or more embodiments, the magnitude of the peak change in i occurring at the electropolymerized phenol oxidation peak potential in the square wave voltammogram linearly correlates with the concentration of the phenol in the first solution ranging from about 0.05 μM to 5 μM.

In one or more embodiments, the linear relationship between the magnitude of the peak change in i occurring at the electropolymerized phenol oxidation peak potential in the square wave voltammogram and the concentration of the phenol in the first solution is defined by a linear equation, and the slope of the linear equation is at least 250 μA μM$^{-1}$.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
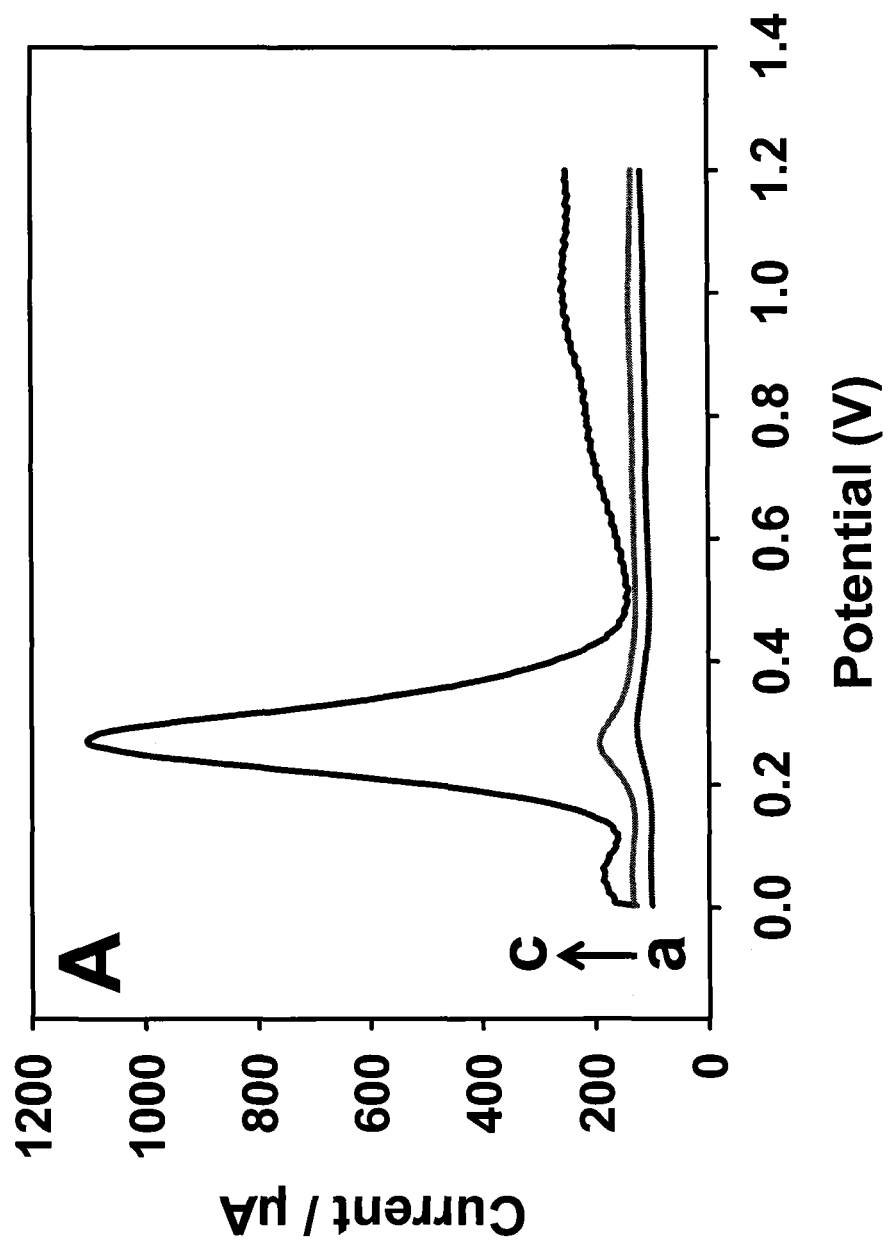
FIG. 1 is a graphical presentation of the square wave voltammograms of the GCE system represented by line (a), the CPE system represented by line (b), and the GPE system represented by line (c) that were charged in 0.2 M $Na_2HPO_4$ and contacted with 0.1 M phosphate buffered saline (PBS, pH 7.2) containing 50 µM phenol to electropolymerize the phenol on the charged surface in open circuit fashion for 60 seconds prior to the square wave voltammetry according to Example 2.

The present disclosure incorporates by reference in its entirety the following publication: Azeem Rana and Abdel- Nasser Kawde, Open-Circuit Electrochemical Polymerization for the Sensitive Detection of Phenols, Electroanalysis, Article first published online: 25 Nov. 2015, DOI: 10.1002/elan.201500603.

The present disclosure provides a method of determining a concentration of phenol and/or a phenol derivative in a first solution containing the phenol and/or the phenol derivative. The method includes (a) subjecting a graphite pencil electrode system to cyclic voltammetry in a second solution, wherein the graphite pencil electrode system comprises a graphite pencil working electrode, a counter electrode, and a reference electrode, and wherein a surface of the graphite pencil working electrode is charged by the cyclic voltammetry to form a charged surface, (b) contacting the charged surface of the graphite pencil working electrode with the first solution for a sufficient period of time to electropolymerize the phenol and/or the phenol derivative on the charged surface of the graphite pencil working electrode in open circuit fashion, and (c) determining the concentration of the phenol and/or the phenol derivative in the first solution, wherein the amount of the electropolymerized phenol and/or the electropolymerized phenol derivative formed on the charged surface of the graphite pencil working electrode correlates with the concentration of the phenol and/or the phenol derivative in the first solution.

In some embodiments, the first solution comprises at least one selected from the group consisting of waste water, lake water, river water, ground water, produced water, a refinery industry effluent, a chemical industry effluent, and a paper industry effluent. These first solutions may be buffered prior to determining a concentration of phenol and/or a phenol derivative. In some embodiments, the pH of the first solution is about 3-14, preferably about 4-12, preferably about 5-10, or more preferably about 6-8. Examples of the first solution, without limitation, include an acetate buffer solution, pH 3-5; a NaOH solution, pH 9-14; and preferably a phosphate buffered saline (PBS), pH 7-9.

The phenol derivative includes, without limitation, an alkylphenol, a catechol, a trihydroxybenzene, a bisphenol, a hydroxybiphenyl, a derivative and a combination thereof. Non-limiting examples of the phenol derivative of which concentrations may be determined by the disclosed method include 4-nonylphenol, 4-octylphenol, 4-tert-octylphenol, 2-aminophenol, 3-aminophenol, 4-aminophenol, 3-methylphenol, 3-nitrophenol, 1,3-dihydroxybenzene, acetaminophen, 1,2-dihydroxybenzene, 1,4-dihydroxybenzene, 1,3,5-trihydroxybenzene, and 1,2,3-trihydroxybenzene.

The electrode system of the present disclosure may be a 3-electrode system comprising a working electrode, a counter electrode, and a reference electrode.

In a preferred embodiment, the working electrode is a graphite pencil electrode, more preferably a disposable graphite pencil electrode. In one embodiment, the pencil graphite substrate of the graphite pencil electrode is made from beneficiated graphite. In another embodiment, the pencil graphite substrate of the graphite pencil electrode is made from milled graphite. In still another embodiment, the pencil graphite substrate of the graphite pencil electrode is made from intercalated graphite, or graphite intercalation compound, non-limiting examples of which include $MC_8$ (M=K, Rb and Cs), $MC_6$ (M=$Li^+$, $Sr^{2+}$, $Ba^{2+}$, $Eu^{2+}$, $Yb^{3+}$, and $Ca^{2+}$), graphite bisulfate, and halogen-graphite compounds.

In other embodiments, the working electrode may be a stainless steel electrode, a titanium electrode, a titanium-base tin dioxide electrode, or a molybdenum electrode.

In the electrode system of the present disclosure, the counter electrode, along with the working electrode, provides a circuit over which current is measured. The potential of the counter electrode can be adjusted to balance the reaction occurring at the working electrode. The counter electrode can be made of a material that does not react with the bulk of the second or the third solution and is conductive. The counter electrode of the present disclosure can be fabricated from a conducting or semiconducting material such as platinum, gold, or carbon.

In the electrode system of the present disclosure, the reference electrode provides a stable and well-known electrode potential, against which the potential of the working electrode is measured. The potential of the reference electrode in the electrochemical instrument of the present disclosure is defined as zero ("0"). The potential of the working electrode lower than the reference electrode means the potential is negative, and the potential of the working electrode higher than the reference electrode means the potential is positive. The stability of the reference electrode in the disclosed electrode system is maintained by not passing current over it. The counter electrode passes all the current needed to balance the current observed at the working electrode. In one embodiment, the reference electrode is an Ag/AgCl reference electrode. In another embodiment, the reference electrode is a hydrogen electrode. In another embodiment, the reference electrode is a saturated calomel electrode. In another embodiment, the reference electrode is a copper-copper (II) sulfate electrode. In still another embodiment, the reference electrode is a palladium-hydrogen electrode.

In one embodiment, the electrode system of the present disclosure can have more than three electrodes. For example, it can have two distinct and separate working electrodes, at least one of which is preferably the graphite pencil electrode, and which can be used to scan or hold potentials independently of each other. Both of the electrodes are balanced by a single reference and counter combination for an overall four electrode design.

In a preferred embodiment, the graphite pencil electrode system is subjected to cyclic voltammetry in a second solution such that a surface of the graphite pencil working electrode is charged. The surface area of the charged surface of the graphite pencil working electrode may vary, depending on the concentration of the phenol and/or the phenol derivative in the first solution and a desirable extent of coverage of the charged surface by the electropolymerized phenol and/or the electropolymerized phenol derivative following the contacting of the charged surface of the graphite pencil working electrode with the first solution in open circuit fashion. In a preferred embodiment, at least 50%, at least 65%, at least 75%, or at least 90% of the total surface area of the graphite pencil working electrode is contacted with the second solution to be charged, and substantially all of the charged surface area of the graphite pencil working electrode is subsequently contacted with the first solution in open circuit fashion to form the electropolymerized phenol and/or the electropolymerized phenol derivative on the charged surface.

The second solution preferably comprises at least one phosphate salt, more preferably at least one phosphate dibasic salt, such as $Na_2HPO_4$ and $K_2HPO_4$ at a concentration of 0.05-1 M, or 0.1-0.8 M, or 0.15-0.6 M, or 0.2-0.4 M, or at least one metal hydroxide, such as NaOH and KOH at a concentration of 0.05-2 M, 0.1-1.5 M, or 0.5-1 M.

In some embodiments, the cyclic voltammetry has a potential range of 0.6-4 V, or 0.8-3.5 V, preferably 1-3 V, or more preferably 1.3-1.9 V.

In some embodiments, the cyclic voltammetry has 20-80, or 30-70, or preferably 40-60, or more preferably 50 voltammetric cycles.

In some embodiments, the cyclic voltammetry has a scan rate of 50-200 mV/s, or 60-150 mV/s, or preferably 70-120 mV/s, or more preferably 90-110 mV/s, or more preferably 100 mV/s.

In another embodiment, the electrode system may be subjected to differential pulse voltammetry to charge a surface of the working electrode.

Once the surface of the working electrode is charged by the cyclic voltammetry or the differential pulse voltammetry, the charged surface of the working electrode is preferably contacted with the first solution containing the phenol and/or the phenol derivative in less than 20 minutes after forming the charged surface, preferably in less than 15 minutes, more preferably in less than 10 minutes, more preferably in less than 5 minutes, or more preferably immediately, since the charge on the charged surface of the working electrode may be lost rapidly, for example, when the charged working electrode is stored in air, water, or a phosphate buffered saline (pH 7.2). In some embodiments, substantially all of the charge is lost after 30 minutes of the storage and about 30-80%, or about 40-70%, or about 50-60% of the charge is lost after 15 minutes of the storage. The contacting of the charged surface of the working electrode with the first solution is done in open circuit fashion, i.e. the working electrode is not connected to a Potentiostat and there is no current passing through the working electrode, preferably accompanied by stirring the first solution. For example, the charged surface of the working electrode disconnected from a Potentiostat may be dipped into the first solution while the first solution is being stirred. During the contacting, the phenol and/or the phenol derivative in the first solution are electropolymerized through the electrooxidation of the phenol and/or the phenol derivative on the charged surface of the working electrode, forming a polymeric film covering the charged surface of the working electrode. Depending on the concentration of the phenol and/or the phenol derivative in the first solution, the contacting time, and the amount of the charge on, and the surface area of, the charged surface of the working electrode, the amount of the electropolymerized phenol (e.g. poly(phenyleneoxide)) and/or the electropolymerized phenol derivative formed on the charged surface of the working electrode may vary, the polymeric film comprising the electropolymerized phenol and/or the electropolymerized phenol derivative may cover 1-100%, preferably 10-90%, preferably 20-80%, or more preferably 30-70% of the charged surface of the working electrode, and the thickness of the polymeric film comprising the electropolymerized phenol and/or the electropolymerized phenol derivative may vary in the range of 1-400 nm, or 10-350 nm, or 50-300 nm, or 80-250 nm, or 100-200 nm, or 120-150 nm. In some embodiments, the contact time is about 30-250 seconds, or about 40-200 seconds, or preferably about 50-150 seconds, or more preferably about 60-120 seconds.

The polymeric film comprising the electropolymerized phenol formed on the charged surface of the working electrode is relatively stable as measured by, for example, the magnitude of the peak change in oxidation current of the electropolymerized phenol at its oxidation peak potential from square wave voltammetry described below. In some embodiments, no greater than 50%, no greater than 40%, no greater than 30%, or no greater than 25% of the electropolymerized phenol in the polymeric film formed on the charged surface of the graphite pencil working electrode is lost at least 3 hours, or at least 5 hours, or at least 7 hours, or at least 10 hours after the end of the contacting of the charged surface of the graphite pencil working electrode with the first solution in open circuit fashion to form the electropolymerized phenol on the charged surface of the graphite pencil working electrode. The electropolymerized phenol in the polymeric film formed on the charged surface of the graphite pencil working electrode may be lost through detachment of the polymeric film or a portion thereof from the charged surface of the graphite pencil working electrode, dissolution of the electropolymerized phenol in a storage solution (e.g. 0.1 M phosphate buffered saline (pH 7.2)) of the graphite pencil working electrode following the open circuit electropolymerization of the phenol on the charged surface of the graphite pencil working electrode and prior to the determination of the phenol concentration in the first solution, de-polymerization, degradation, and/or other chemical transformations of the electropolymerized phenol. With every other condition for the electropolymerization of the phenol and/or the phenol derivative being the same, such as the electrode system used, the method and the condition for the charging of the surface of the working electrode, the composition of the first solution, the time interval between the end of the charging of the working electrode and the start of the contacting of the charged surface of the working electrode with the first solution, the time of the contacting in open circuit fashion, etc., the amount of the electropolymerized phenol and/or the electropolymerized phenol derivative formed on the charged surface of the working electrode correlates with the concentration of the phenol and/or the phenol derivative in the first solution. Thus, measuring the amount of, or the electrochemical signal intensity (e.g. voltammetric signal, more specifically the peak change in oxidation current) from, the electropolymerized phenol and/or the electropolymerized phenol derivative can be used as a basis for determining the concentration of the phenol and/or the phenol derivative in the first solution. Since the electropolymerized phenol and/or the electropolymerized phenol derivative is on the surface of the working electrode, their amounts can be conveniently quantified by electrochemical means, preferably by voltammetry, preferably by differential pulse voltammetry, preferably by cyclic voltammetry, or more preferably by square wave voltammetry.

In a preferred embodiment, the square wave voltammetry is performed by contacting the graphite pencil working electrode having the electropolymerized phenol and/or the electropolymerized phenol derivative formed on the charged surface, the counter electrode, and the reference electrode with a third solution. The square wave voltammetry includes (a) applying a pulsed potential to the graphite pencil working electrode while sweeping the potential of the graphite pencil working electrode from a potential that is less than an oxidation peak potential of the electropolymerized phenol and/or the electropolymerized phenol derivative in the third solution positively to a potential that is at least the oxidation peak potential of the electropolymerized phenol and/or the electropolymerized phenol derivative in the third solution, and (b) recording the amount of a forward pulse current and a reverse pulse current during each square wave cycle.

In square wave voltammetry, the current at the working electrode is measured while the potential between the working electrode and the reference electrode is swept linearly in time. The potential waveform can be viewed as a superposition of a regular square wave onto an underlying staircase. Preferably, the current is sampled at two times—once at the end of the forward potential pulse and again at the end of the reverse potential pulse (in both cases immediately before the potential direction is reversed). As a result of this current sampling technique, the contribution to the current signal resulting from capacitive (sometimes referred to as non-faradaic or charging) current is minimal. As a result of having current sampling at two different instances per square wave cycle, two current waveforms are collected—both have diagnostic value, and are therefore preserved. When viewed in isolation, the forward and reverse current waveforms mimic the appearance of a cyclic voltammogram. Despite both the forward and reverse current waveforms having diagnostic value, it is customary in square wave voltammetry for the potentiostat software to plot a differential current waveform derived by subtracting the reverse current waveform from the forward current waveform. This differential curve is then plotted against the applied potential. Peaks in the differential current vs. applied potential plot are indicative of redox processes, and the magnitudes of the peaks (peak heights) in this plot are proportional to the concentrations of the various redox active species determined by the square wave voltammetry.

The third solution which is the square wave voltammetry medium is preferably an aqueous solution comprising electrolytes, such as a phosphate buffered saline, with a pH of 2-10, or 4-9, or preferably 6-8, or more preferably 7.0-7.2.

In some embodiments, the amplitude of the pulsed potential is about 0.01-0.20 V, preferably about 0.01-0.15 V, more preferably about 0.02-0.10 V, more preferably about 0.04-0.08 V, more preferably about 0.05-0.07 V.

In some embodiments, the voltage step of the square wave voltammetry is about 2-10 mV, preferably about 3-8 mV, or more preferably about 3-5 mV.

In some embodiments, the frequency of the pulsed potential of the square wave voltammetry is about 10-100 Hz, preferably about 20-80 Hz, or more preferably about 30-60 Hz.

In some embodiments, the oxidation peak potential of the electropolymerized phenol in the third solution lies in the range of about 0.0-1.0 V, or about 0.1-0.8 V, or about 0.2-0.6 V, or about 0.2-0.4 V.

In some embodiments, the lowest phenol concentration in the first solution determined or detected via the square wave voltammetry is about 3-60 nM, or about 5-50 nM, or about 7-30 nM, or about 10-25 nM.

The disclosed method advantageously detects phenol and its derivative and measures their concentrations without interference from common metallic ions, such as $Co^{2+}$, $Cu^{2+}$, $Ca^{2+}$, $Na^+$, $K^+$, $Pb^{2+}$, and $Cd^{2+}$, which can exist in phenol or its derivative contaminated water samples, because as cations they are not oxidized volumetrically.

To quantify the concentration of the phenol and/or the phenol derivative in the first solution, the square wave voltammetry can further comprise plotting the difference in current between the forward pulse current and the reverse pulse current during each square wave cycle, the difference in current represented by i, against the applied potential of the graphite pencil working electrode to obtain a square wave voltammogram, and measuring the magnitudes of peak changes in i (peak heights) in the square wave voltammogram. If there is a mixture of phenol and its derivative (e.g. an alkyl phenol), or a mixture of phenol derivatives in the first solution, their respective electropolymerized products may undergo oxidation within the range of the applied potential of the graphite pencil working electrode during the square wave voltammetry. The oxidation current peaks of the electropolymerized products may be distinguished from one another and the concentration of the corresponding phenol and/or the phenol derivative in the first solution can be reliably determined from the square wave voltammogram if there are sufficient separations among the oxidation peak potentials of the electropolymerized products in the third solution. If the separations are not sufficient or the oxidation current peaks of the electropolymerized products are not fully resolved, the presence of phenol and its derivative, or different phenol derivatives in the first solution may be detected but their respective concentrations may not be reliably determined. In some embodiments, the magnitude of the peak change in i occurring at the electropolymerized phenol oxidation peak potential in the square wave voltammogram linearly correlates with the concentration of the phenol in the first solution ranging from about 0.02 μM to 10 μM, or from about 0.05 μM to 8 μM, or from about 0.05 μM to 5 μM, from about 0.2 μM to 5 μM, or from about 0.4 μM to 3 μM, in the first solution.

In some embodiments, the linear relationship between the magnitude of the peak change in i occurring at the electropolymerized phenol oxidation peak potential in the square wave voltammogram and the concentration of the phenol in the first solution is defined by a linear equation, and the slope of the linear equation is at least 150 $\mu A\ \mu M^{-1}$, at least 200 $\mu A\ \mu M^{-1}$, at least 250 $\mu A\ \mu M^{-1}$, at least 500 $\mu A\ \mu M^{-1}$, at least 800 $\mu A\ \mu M^{-1}$, at least 1000 $\mu A\ \mu M^{-1}$, or at least 1300 $\mu A\ \mu M^{-1}$.

Having generally described this invention, a further understanding can be obtained by reference to certain specific examples which are provided herein for purposes of illustration only and are not intended to be limiting unless otherwise specified.

Example 1

Methods and Materials

1. Reagents

All chemicals were analytical reagent grade and used without further purification. Phenol, monosodium phosphate, monopotassium phosphate and disodium phosphate were obtained from Sigma Aldrich® (USA). Hi-polymer graphite pencil HB black leads were obtained from Pentel (Japan). All leads had a total length of 60 mm and a diameter of 0.5 mm and were used as received.

2. Apparatus and Procedures

A Jedo mechanical pencil (Korea) was used as a holder for both uncharged and charged graphite pencil leads. Electrical contact with the lead was achieved by soldering a copper wire to the metallic part that holds the lead in place inside the pencil. The pencil was fixed vertically with 15 mm of the pencil lead protruding outside, 10 mm of which was immersed in a solution that the graphite pencil electrode contacted. Such length corresponds to an electrode geometric area of 16.10 $mm^2$. A CHI 660C electrochemical analyzer/workstation (CH Instruments, USA) was used for the entire electrochemical work. The electrochemical cell contained the graphite pencil electrode (GPE) as the working electrode, a Pt wire counter electrode, and an Ag/AgCl (Sat. KCl) reference electrode.

3. Graphite Pencil Electrode (GPE) Charging

The 10 mm protruding pencil lead of the GPE, the Ag/AgCl reference electrode, and the Pt wire counter electrode were immersed in a 0.2 M $Na_2HPO_4$ solution or a 0.1 M or 0.8 M NaOH solution contained in an electrochemical cell. Cyclic voltammetry (CV) was applied to charge a GPE surface, with the following conditions: 1.3-1.9 V potential range, 50 CV segments, and 100 mV/s scan rate. The charged GPE was washed by gently dipping the charged GPE into deionized water twice, and was promptly used for the electropolymerization of phenol and the electrochemical detection of the phenol described below.

4. Open Circuit Electropolymerization of Phenol

The charged graphite pencil electrode (CGPE) surface was dipped in a 0.1 M phosphate buffered saline (PBS, pH 7.2) containing a certain concentration of phenol without the GPE being connected to a Potentiostat for electropolymerization of the phenol on the charged surface of the GPE in open circuit fashion. The open circuit electropolymerization of the phenol was allowed to last preferably for 60 seconds, or more preferably for 120 seconds, while the phenol containing 0.1 M PBS (pH 7.2) was being stirred.

5. Electrochemical Detection of Phenol

The phenol concentration in the above 0.1 M phosphate buffered saline (pH 7.2) was determined by square wave voltammetry (SWV) performed with the GPE having the electropolymerized phenol formed on the charged surface as the working electrode and a 0.1 M phosphate buffered saline at a preferred pH of 7.0-7.2 (without phenol) as the SWV medium. Specifically, the GPE having the electropolymerized phenol formed on the charged surface was dipped in the 0.1 M phosphate buffered saline (pH 7.0-7.2). After a 10 s rest period without stirring the 0.1 M phosphate buffered saline (pH 7.0-7.2), the square wave voltammetry was carried out with the GPE having the electropolymerized phenol formed on the charged surface as the working electrode, the Ag/AgCl (Sat. KCl) reference electrode, and the Pt wire counter electrode.

Example 2

Figure 2:
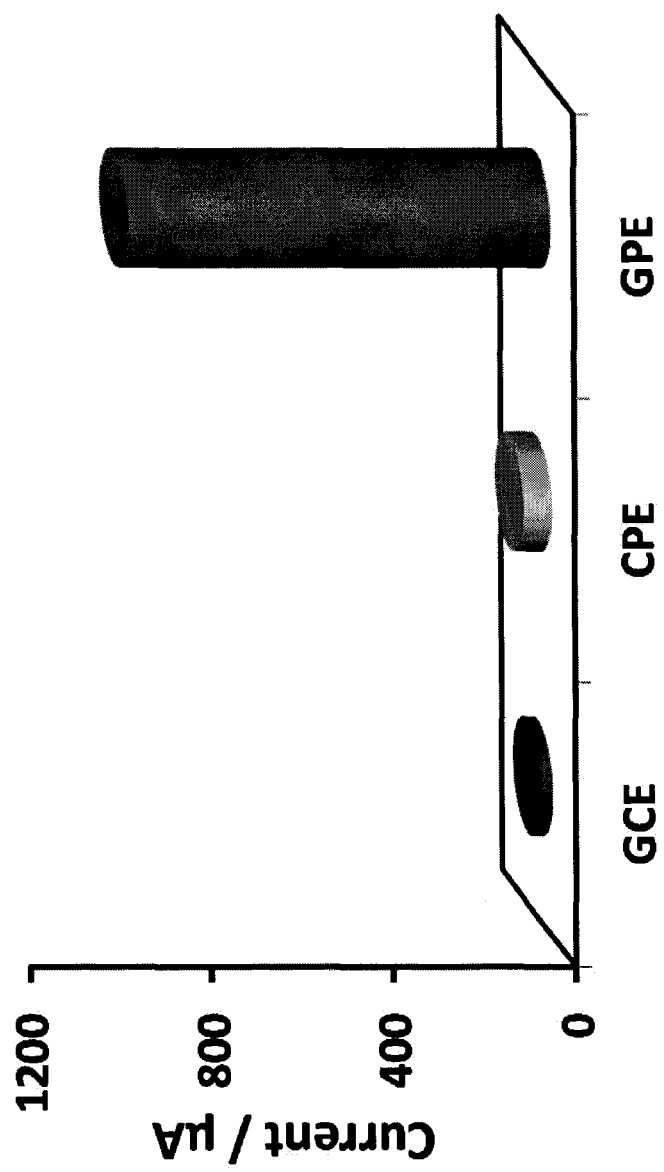
FIG. 2 is a graphical presentation of the magnitudes of the peak change in the oxidation current at the electropolymerized phenol oxidation peak potential with the GCE system, the CPE system, and the GPE system derived from the square wave voltammograms of FIG. 1 according to Example 2.

Comparison of the Graphite Pencil Electrode (GPE) with a Glassy Carbon Electrode (GCE) and a Carbon Paste Electrode (CPE) as the Working Electrode for the Charging, the Open Circuit Electropolymerization of Phenol, and the Electrochemical Detection of Phenol Using Square Wave Voltammetry Following the charging of a surface of the GPE by cyclic voltammetry in the 0.2 M $Na_2HPO_4$ solution as described above, the charged surface of the GPE was contacted with a 0.1 M phosphate buffered saline (pH 7.2) containing 50 µM phenol to electropolymerize the phenol on the charged surface in open circuit fashion for 60 seconds, and then square wave voltammetry was performed with the GPE having the electropolymerized phenol formed on the charged surface as the working electrode, the Ag/AgCl (Sat. KCl) reference electrode, and the Pt wire counter electrode in a 0.1 M phosphate buffered saline (pH 7.2). For comparison, a surface of a glassy carbon electrode (GCE) and a surface of a carbon paste electrode (CPE) were likewise charged, their respective charged surfaces were likewise contacted with the 0.1 M phosphate buffered saline (pH 7.2) containing 50 µM phenol for electropolymerization of the phenol on the respective charged surfaces in open circuit fashion, and each of the resulting electrodes having the electropolymerized phenol formed on their respective charged surfaces was likewise subjected to the square wave voltammetry as the working electrode, together with the Ag/AgCl (Sat. KCl) reference electrode and the Pt wire counter electrode under the same conditions as the aforementioned graphite pencil electrode system. FIG. 1 shows the square wave voltammograms obtained with the GPE system (line c), the GCE system (line a), and the CPE system (line b), where "Current" is the difference in current between the two current measurements during each square wave cycle, one at the end of the forward pulse, and the other at the end of the reverse pulse, and "Potential" is the potential applied to the working electrode GPE, GCE, or CPE. Although all of the three electrode systems produced well defined oxidation current peaks at the electropolymerized phenol oxidation peak potential, the magnitude of the peak change in, or the peak height of, the oxidation current at the electropolymerized phenol oxidation peak potential with the GPE system was about 40.03 times and 15 times higher than that with the GCE and CPE system, respectively, as shown in FIG. 2.

Example 3

Figure 3:
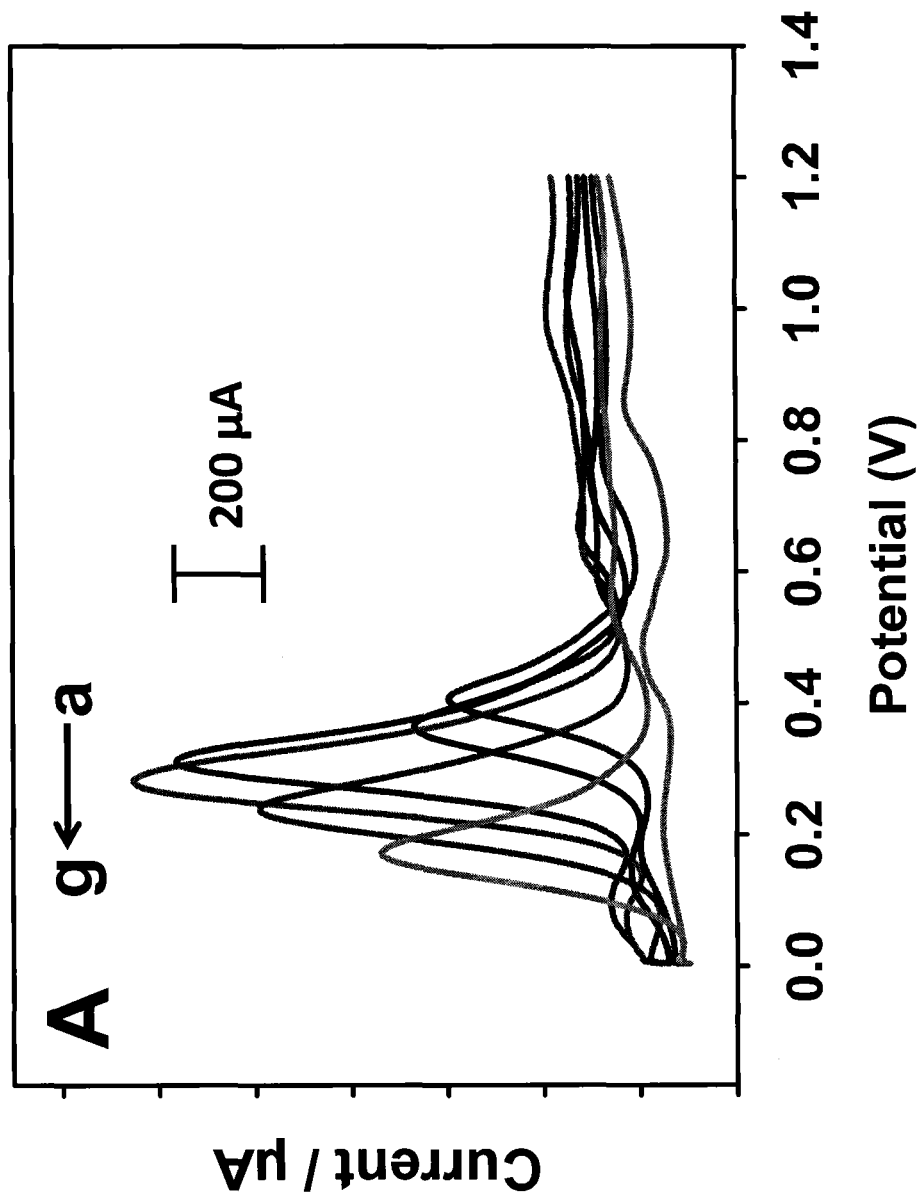
FIG. 3 is a graphical presentation of the square wave voltammograms with the GPE system that was charged in 0.8 M NaOH and contacted with 0.1 M phosphate buffered saline (pH 7.2) containing 50 µM phenol to electropolymerize the phenol on the charged surface in open circuit fashion for 60 seconds prior to the square wave voltammetry, the medium of which was 0.1 M phosphate buffered saline with a pH of a) 4.0, b) 4.8, c) 5.6, d) 6.4, e) 7.2, f) 8.0, and g) 8.8 according to Example 3.
Figure 4:
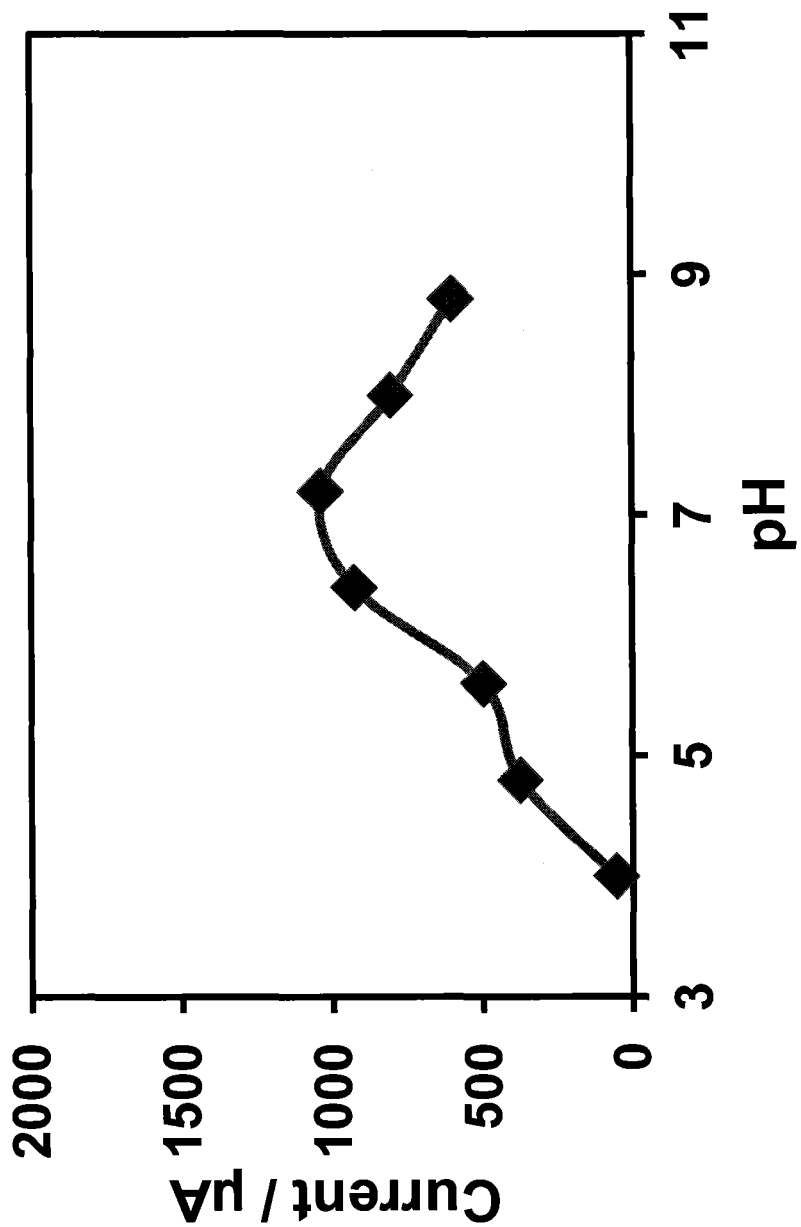
FIG. 4 is a graphical presentation of the relationship between the oxidation current peak height of the electropolymerized phenol and the pH of the 0.1 M phosphate buffered saline used as the square wave voltammetry medium derived from the square wave voltammograms of FIG. 3 according to Example 3.
Figure 5:
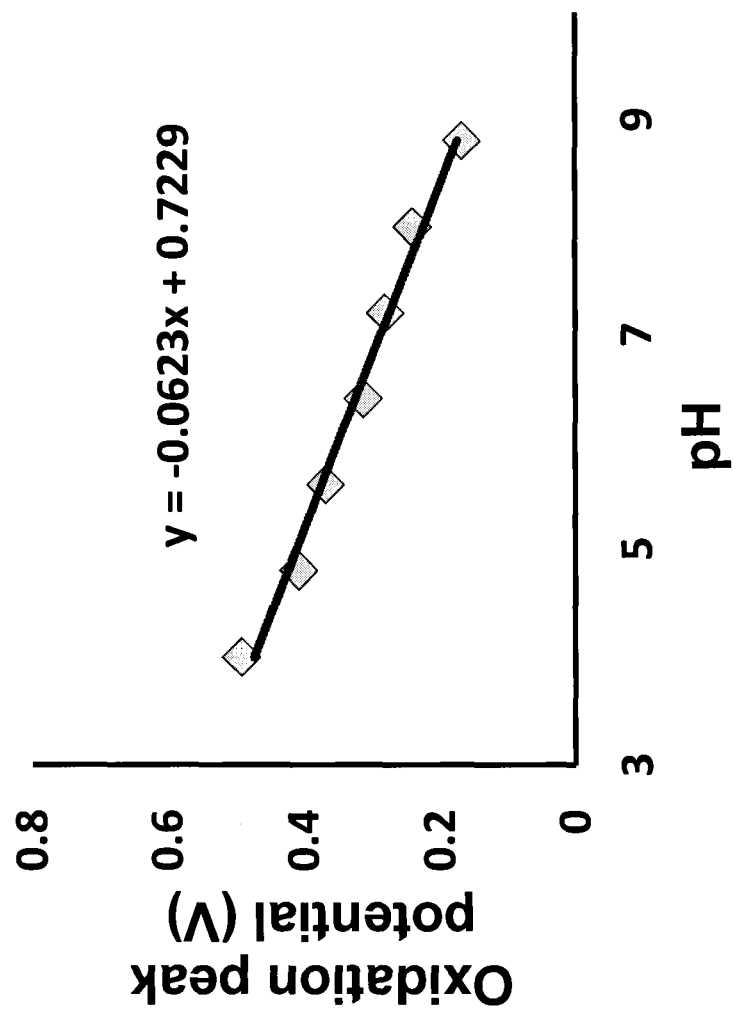
FIG. 5 is a graphical presentation of the relationship between the oxidation peak potential of the electropolymerized phenol and the pH of the 0.1 M phosphate buffered saline used as the square wave voltammetry medium derived from the square wave voltammograms of FIG. 3 according to Example 3.

The Effect of the pH of the SWV Medium on the Electrochemical Detection of Phenol Using the GPE System and SWV In Example 2, the square wave voltammetry was performed by contacting the GPE system with a 0.1 M phosphate buffered saline with the pH of 7.2 as the SWV medium, following the charging of the GPE and electropolymerization of phenol on the charged surface of the GPE in open circuit fashion in a 0.1 M phosphate buffered saline (pH 7.2) containing 50 µM phenol. To determine the effect of the pH of the 0.1 M phosphate buffered saline as the square wave voltammetry medium on the electrochemical detection of phenol, specifically on the electropolymerized phenol oxidation peak potential and the magnitude of the peak change in the oxidation current at the electropolymerized phenol oxidation peak potential, square wave voltammetry was performed by contacting the GPE system with a 0.1 M phosphate buffered saline with a pH of 4.0, 4.8, 5.6, 6.4, 7.2, 8.0, or 8.8, following the charging of the GPE by the cyclic voltammetry in 0.8 M NaOH and the electropolymerization of phenol on the charged surface of the GPE in open circuit fashion in the 0.1 M phosphate buffered saline (pH 7.2) containing 50 µM phenol for 60 seconds. The pH of the 0.1 M phosphate buffered saline used as the SWV medium significantly affected the oxidation peak potential of the electropolymerized phenol, the oxidation peak current of the electropolymerized phenol, and the oxidation current peak height corresponding to the magnitude of the peak change in the oxidation current occurring at the oxidation peak potential of the electropolymerized phenol in the square wave voltammograms shown in FIG. 3. Referring to FIG. 4, the oxidation current peak height of the electropolymerized phenol increased as the pH increased and reached its maximum value at pH 7.2. Further increases in the pH reduced the oxidation current peak height. Referring to FIG. 5, the oxidation peak potential of the electropolymerized phenol decreased linearly with the increasing pH.

Example 4

Figure 6:
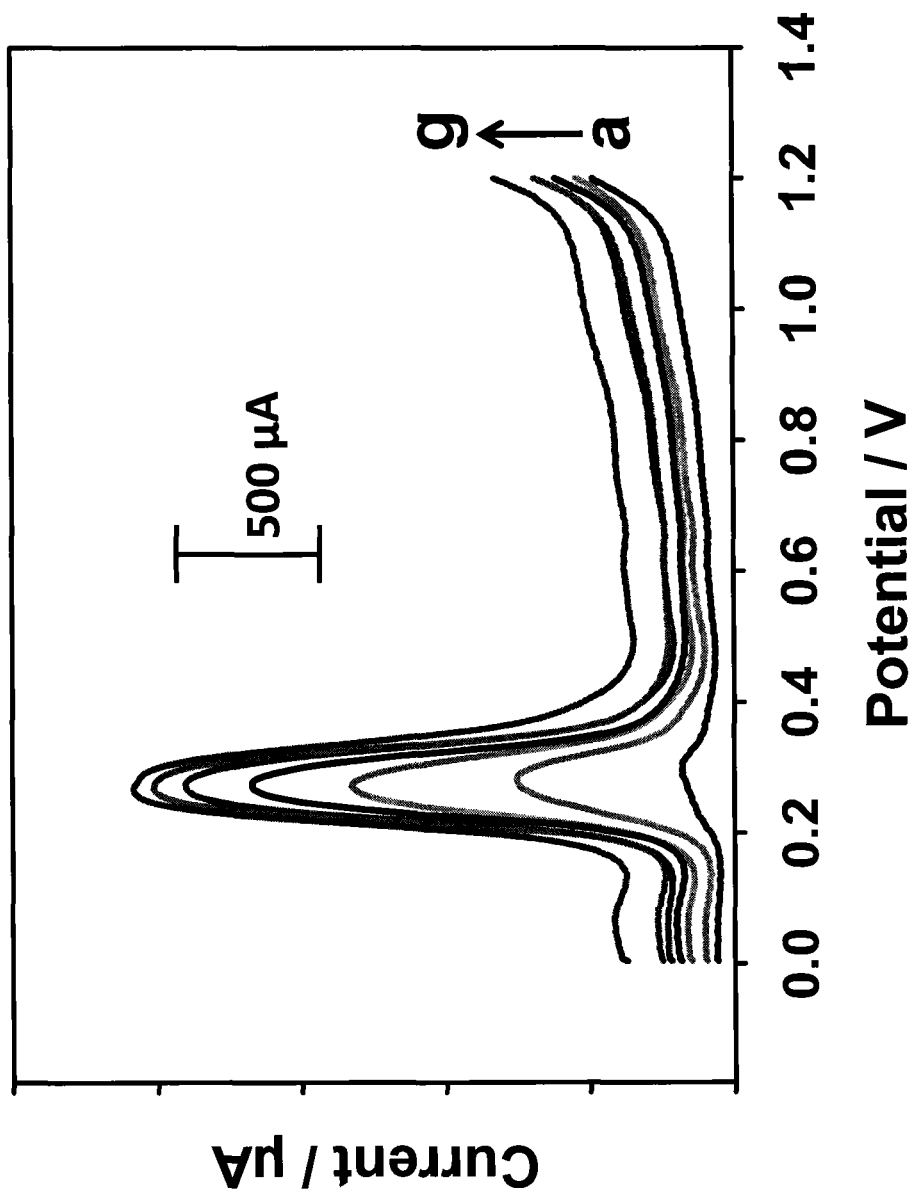
FIG. 6 is a graphical presentation of the square wave voltammograms with the GPE system that was charged in 0.1 M NaOH and contacted with 0.1 M phosphate buffered saline (pH 7.2) containing 2 µM phenol to electropolymerize the phenol on the charged surface of the GPE in open circuit fashion for (a) 15 seconds, (b) 30 seconds, (c) 60 seconds, (d) 90 seconds, (e) 120 seconds, (f) 150 seconds and (g) 180 seconds prior to the square wave voltammetry (SWV) in 0.1 M phosphate buffered saline (pH 7.0) as the SWV medium according to Example 4.
Figure 7:
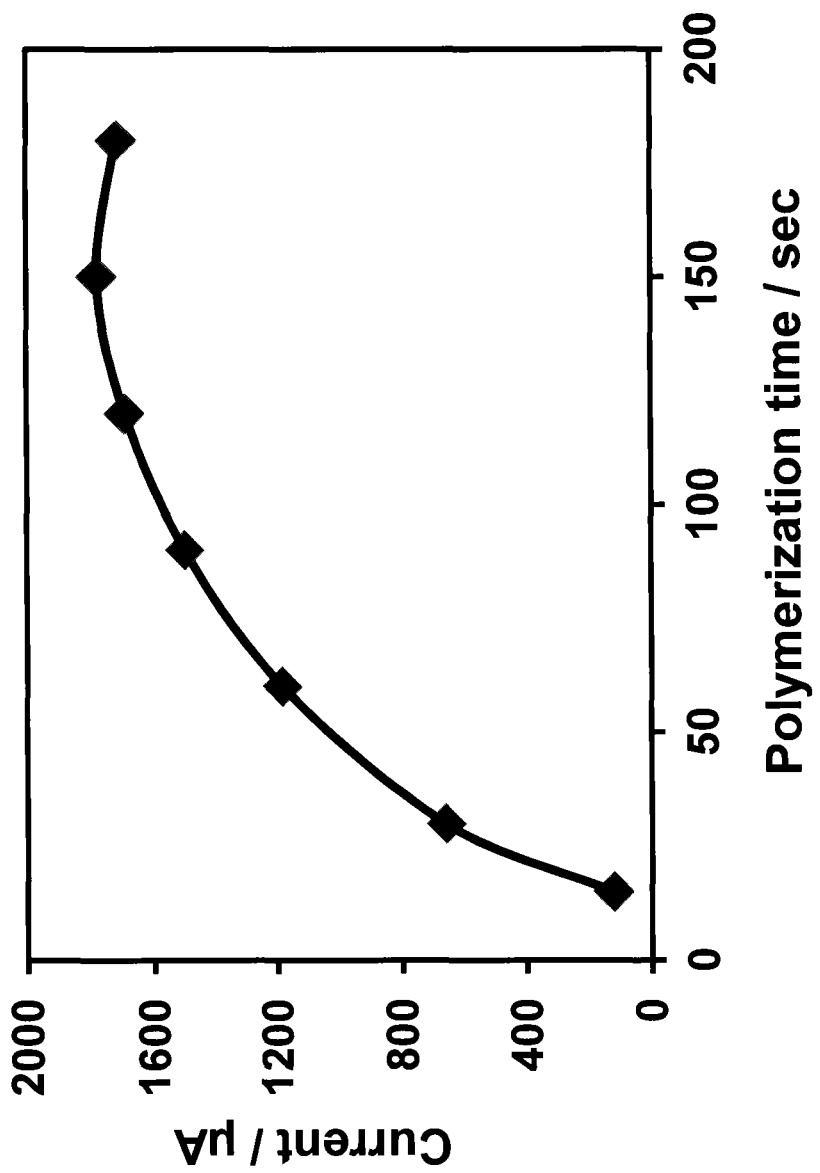
FIG. 7 is a graphical presentation of the relationship between the oxidation current peak height of the electropolymerized phenol and the phenol electropolymerization time derived from the square wave voltammograms of FIG. 6 according to Example 4.

Determination of the Preferred Duration for the Electropolymerization of Phenol and the Preferred SWV Parameters for the Electrochemical Detection of Phenol Using the GPE System The preferred duration for the electropolymerization of phenol on the charged surface of the GPE in open circuit fashion was determined to be 120 seconds, since the oxidation peak current and the peak change in the oxidation current occurring at the oxidation peak potential of the electropolymerized phenol measured by SWV and shown in FIG. 6 and FIG. 7, respectively, increased with an increasing duration for the electropolymerization of phenol up to 120 seconds and then leveled off, with the fixed GPE charging conditions (i.e. 0.1 M NaOH as the charging solution, 1.3-1.9 V charging potential, 50 charging CV segments, and 100 mV/s charging scan rate), the fixed phenol concentration of 2 µM in 0.1 M phosphate buffered saline (pH 7.2) for the open circuit electropolymerization of phenol, and the fixed SWV conditions (i.e. 50 Hz frequency, 0.06 V amplitude, and 0.1 M phosphate buffered saline (pH 7.0) as the SWV medium).

For the SWV, besides the preferred pH of the 0.1 M phosphate buffered saline (as the SWV medium) being 7.0-7.2, other preferred parameters included the amplitude of 0.06 V, the frequency of 50 Hz, the voltage step of 4 mV, and the range of the scanned potential of 0.0-1.2V.

Example 5

Figure 8:
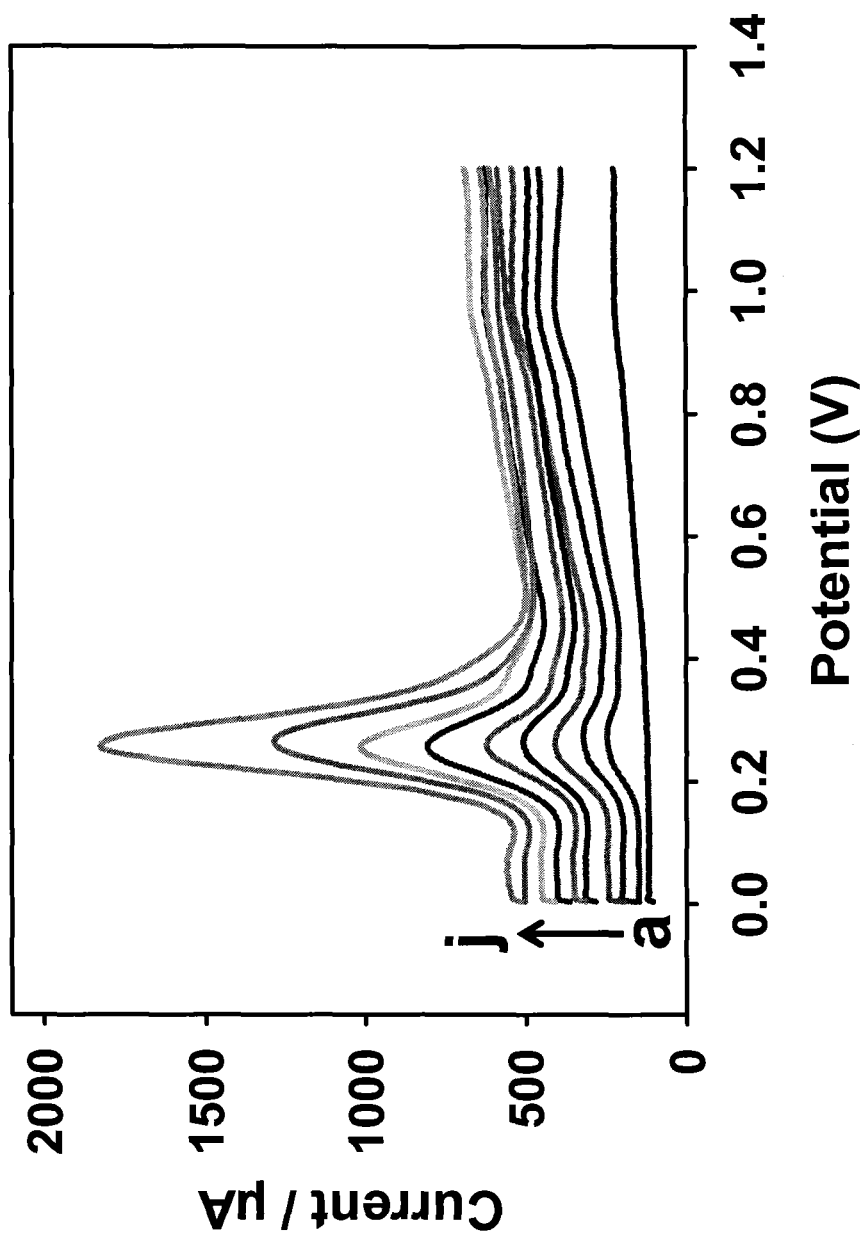
FIG. 8 is a graphical presentation of the square wave voltammograms with the GPE system that was charged in 0.2 M $Na_2HPO_4$ and contacted with one of a series of 0.1 M phosphate buffered salines (pH 7.2) containing the following concentrations of phenol a) 0 µM, b) 0.2 µM, c) 0.3 µM, d) 0.5 µM, e) 0.7 µM, f) 1.0 µM, g) 1.5 µM, h) 2.0 µM, i) 3.0 µM and j) 5.0 µM to electropolymerize the phenol on the charged surface of the GPE in open circuit fashion for 60 seconds prior to the square wave voltammetry in 0.1 M PBS (pH 7.2) as the SWV medium according to Example 5.
Figure 9:
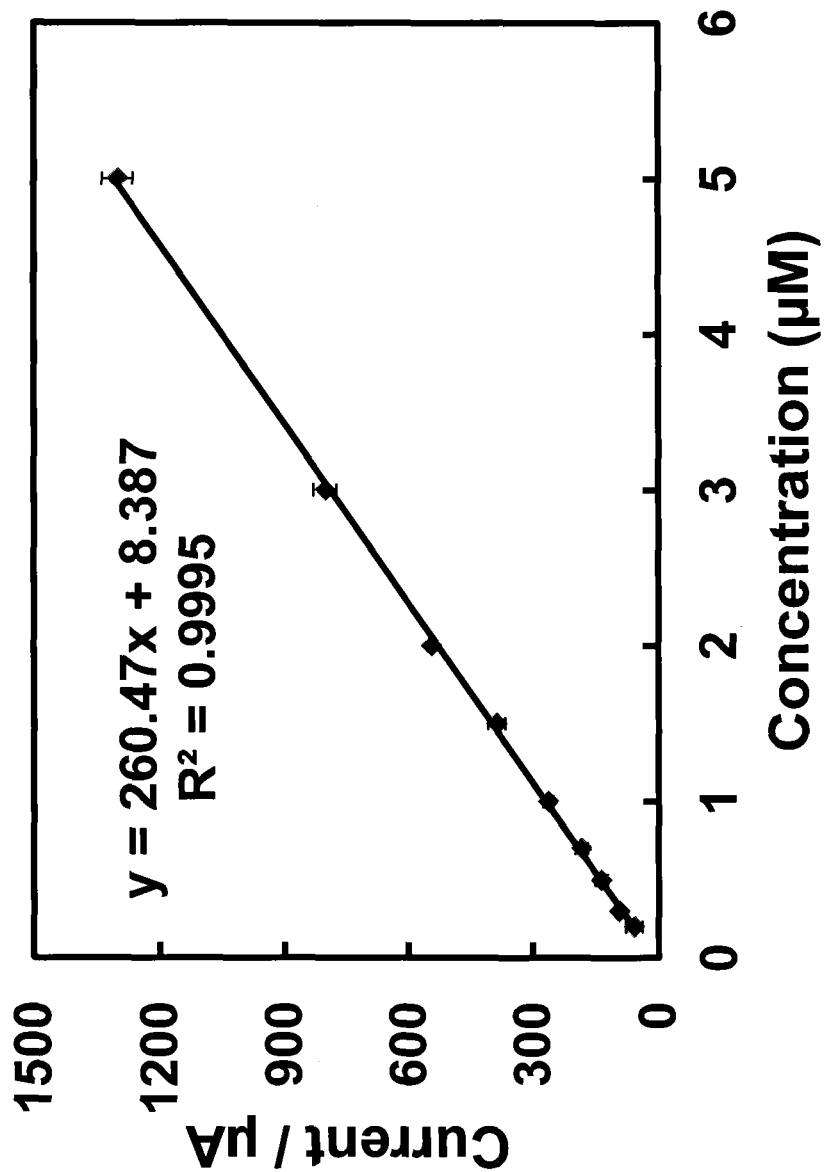
FIG. 9 is a graphical presentation of the linear relationship between the oxidation current peak heights of the electropolymerized phenol derived from the square wave voltammograms of FIG. 8 and the corresponding phenol concentrations according to Example 5, with the coefficient of determination ($R^2$) of 0.9995.

Determination of the Calibration Curve and the Detection Limit for Measuring the Phenol Concentration in a Solution Using the GPE System and SWV Following the charging of the GPE in 0.2 M $Na_2HPO_4$, the charged GPE was contacted with one of a series of 0.1 M phosphate buffered salines (pH 7.2) containing different concentrations of phenol, i.e. 0 µM, 0.2 µM, 0.3 µM, 0.5 µM, 0.7 µM, 1.0 µM, 1.5 µM, 2.0 µM, 3.0 µM and 5.0 µM to electropolymerize the phenol on the charged surface in open circuit fashion for 60 seconds. The resulting GPE system was then subjected to the SWV with the preferred parameters to obtain a calibration curve correlating the voltammetric signals with the phenol concentrations. Referring to the square wave voltammograms in FIG. 8 and the calibration curve in FIG. 9, the oxidation current peak heights at the oxidation peak potential of the electropolymerized phenol in the square wave voltammograms and the phenol concentrations ranging from 0.2 µM to 5 µM in the 0.1 M phosphate buffered saline (pH 7.2) were linearly correlated. The linear equation y=260.47 x+8.387 was obtained by linear regression, with the coefficient of determination ($R^2$) of 0.9995. Thus, in this instance of the current example, the disclosed method exhibited a satisfactory phenol detection sensitivity of 260 µA µ$M^{-1}$ (as indicated by the slope of the linear equation), which was higher than the phenol detection sensitivity displayed by the result shown in FIG. 4 of Example 3, where the maximum peak change in the oxidation current of the electropolymerized phenol formed from the 0.1 M PBS (pH 7.2) containing 50 µM phenol was recorded at just above 1000 µA, because more preferred conditions were used here. The detection limit of phenol using the disclosed GPE system and SWV was 14.67 nM at a signal/noise ratio (S/N) of 3.

Figure 10:
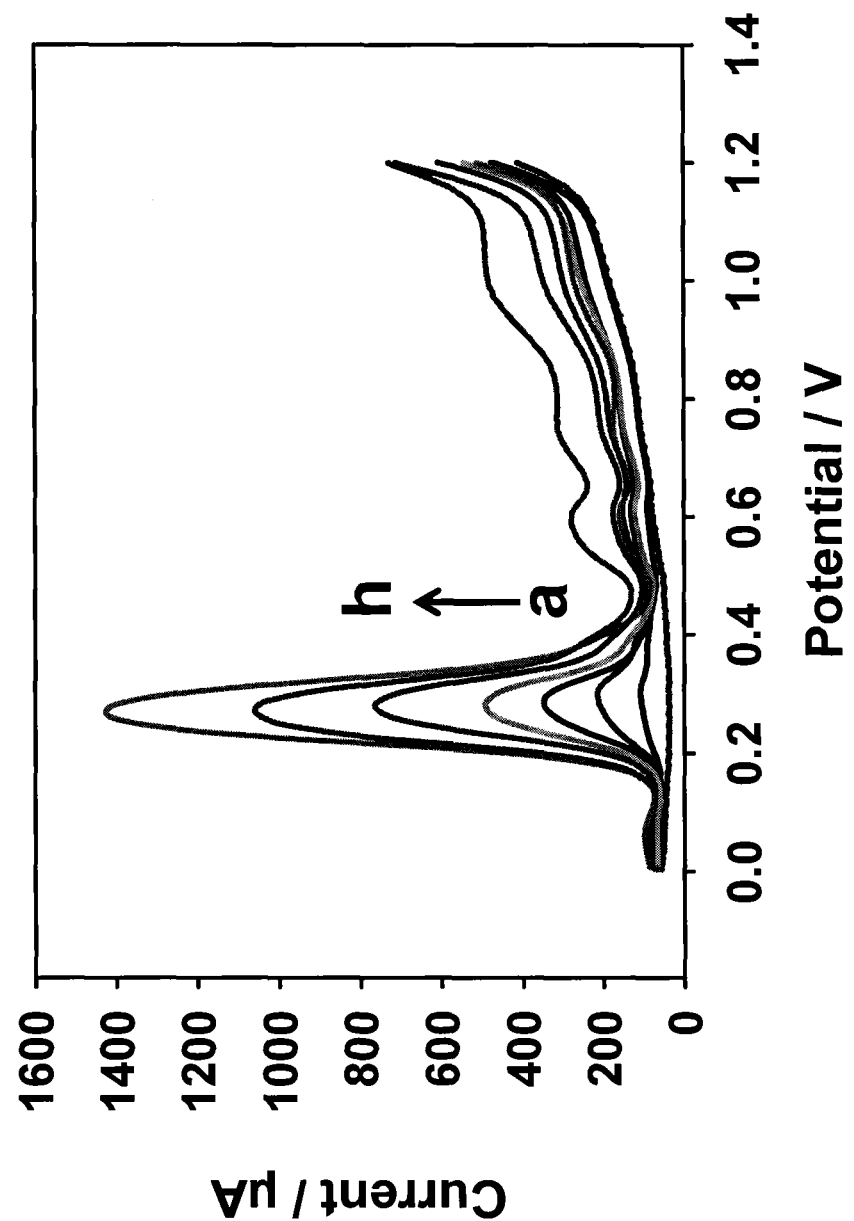
FIG. 10 is a graphical presentation of the square wave voltammograms with the GPE system that was charged in 0.1 M NaOH and contacted with one of a series of 0.1 M PBS (pH 7.2) containing the following concentrations of phenol a) 0 b) 0.05 µM, c) 0.1 µM, d) 0.2 µM, e) 0.3 µM, f) 0.5 µM, g) 0.7 µM, and h) 1.0 µM to electropolymerize the phenol on the charged surface of GPE in open circuit fashion for 120 seconds prior to the square wave voltammetry in 0.1 M PBS (pH 7.0) as the SWV medium according to Example 5.
Figure 11:
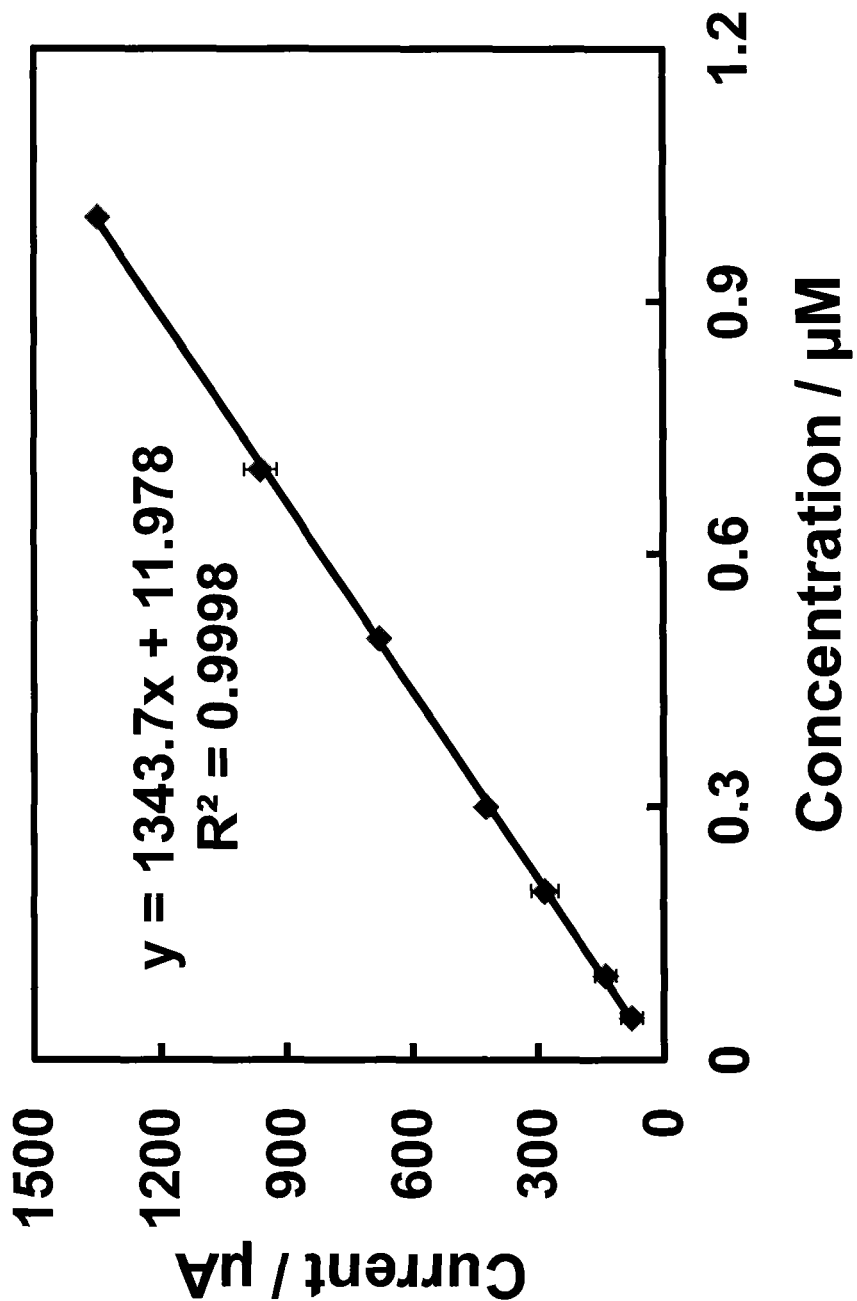
FIG. 11 is a graphical presentation of the linear relationship between the oxidation current peak heights of the electropolymerized phenol derived from the square wave voltammograms of FIG. 10 and the corresponding phenol concentrations according to Example 5, with the coefficient of determination ($R^2$) of 0.9998.

The calibration curve and the detection limit for measuring the phenol concentration were determined in another instance under even more preferred conditions. Specifically, following the charging of the GPE with 0.1 M NaOH as the charging solution, the charged GPE was contacted with one of a series of 0.1 M phosphate buffered salines (pH 7.2) containing different concentrations of phenol, i.e. 0 µM, 0.05 µM, 0.1 µM, 0.2 µM, 0.3 µM, 0.5 µM, 0.7 µM and 1.0 µM to electropolymerize the phenol on the charged surface in open circuit fashion for 120 seconds. The resulting GPE system was then subjected to the SWV with the preferred parameters to obtain a calibration curve correlating the voltammetric signals with the phenol concentrations. Referring to the square wave voltammograms in FIG. 10 and the calibration curve in FIG. 11, the oxidation current peak heights at the oxidation peak potential of the electropolymerized phenol in the square wave voltammograms and the phenol concentrations ranging from 0.05 µM to 1.0 µM in the 0.1 M phosphate buffered saline (pH 7.2) were linearly correlated. The linear equation y=1343.7 x+11.978 was obtained by linear regression, with the coefficient of determination ($R^2$) of 0.9998. Thus, in this instance of the current example, the disclosed method exhibited an even greater phenol detection sensitivity of 1343.7 µA µ$M^{-1}$ (as indicated by the slope of the linear equation) and a lower phenol detection limit of 4.17 nM at a signal/noise ratio (S/N) of 3.

The reproducibility of using the GPE system to determine a phenol concentration in a solution was examined by fabricating six GPEs under the same set of conditions. Small deviations in the oxidation peak current of the electropolymerized phenol were observed with a relative standard deviation (RSD) of 3.76%, indicating an excellent reproducibility.

Example 6

Determination of the Stability of Charge on the Charged Surface of the GPE

Figure 12:
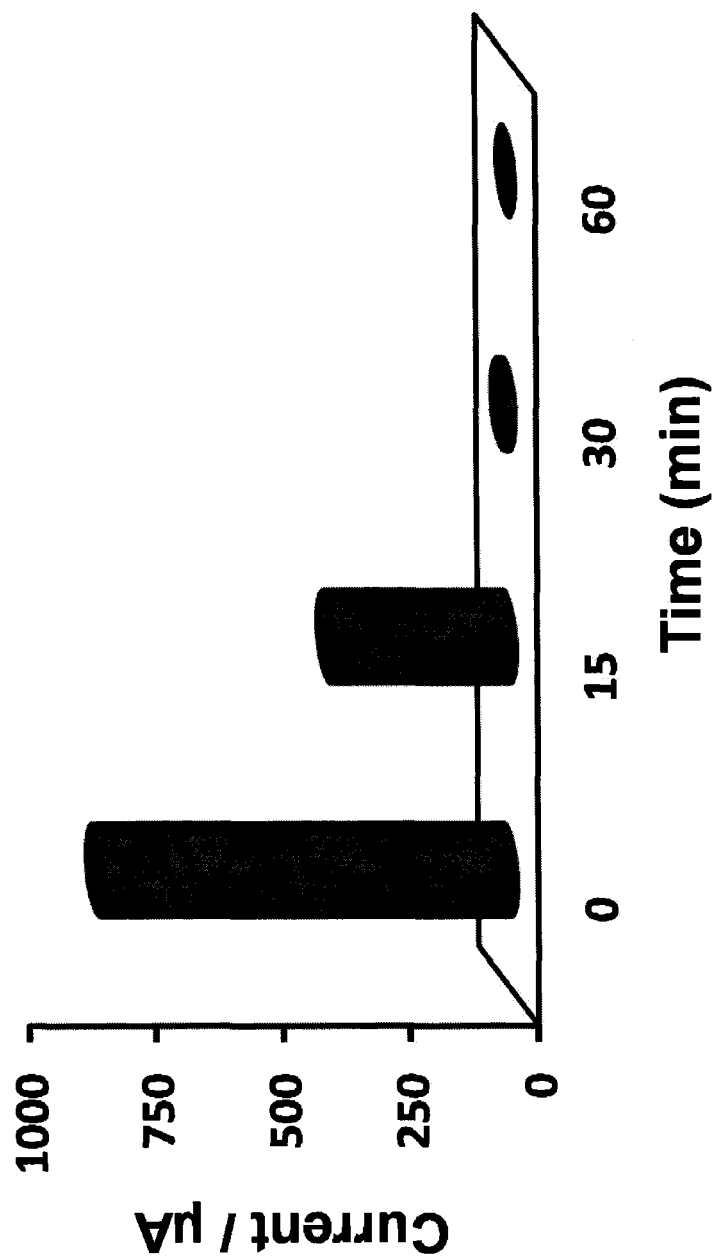
FIG. 12 is a graphical presentation of the relationship between the oxidation current peak height of the electropolymerized phenol determined by square wave voltammetry and the time of the storage of the charged GPE in a phosphate buffered saline (pH 7.2) prior to the contacting of the charged GPE with a phosphate buffered saline containing 50 µM phenol in open circuit fashion to form the electropolymerized phenol on the charged surface of the GPE according to Example 6.

To test the rate of discharge on the charged surface of the GPE, following the charging of the GPE, the charged GPE was stored in a phosphate buffered saline (pH 7.2) for different times (i.e. 0 min, 15 min, 30 min, and 60 min) before contacting a phosphate buffered saline containing 50 µM phenol in open circuit fashion to form the electropolymerized phenol on the charged surface. Afterwards, the SWV was performed to determine the oxidation current peak heights at the oxidation peak potential of the electropolymerized phenol. Referring to FIG. 12, the charge on the charged surface of the GPE was lost rapidly, as the oxidation current peak height at the oxidation peak potential of the electropolymerized phenol was reduced 50% after 15 minutes of the storage and became zero after one hour of the storage.

Example 7

Figure 13:
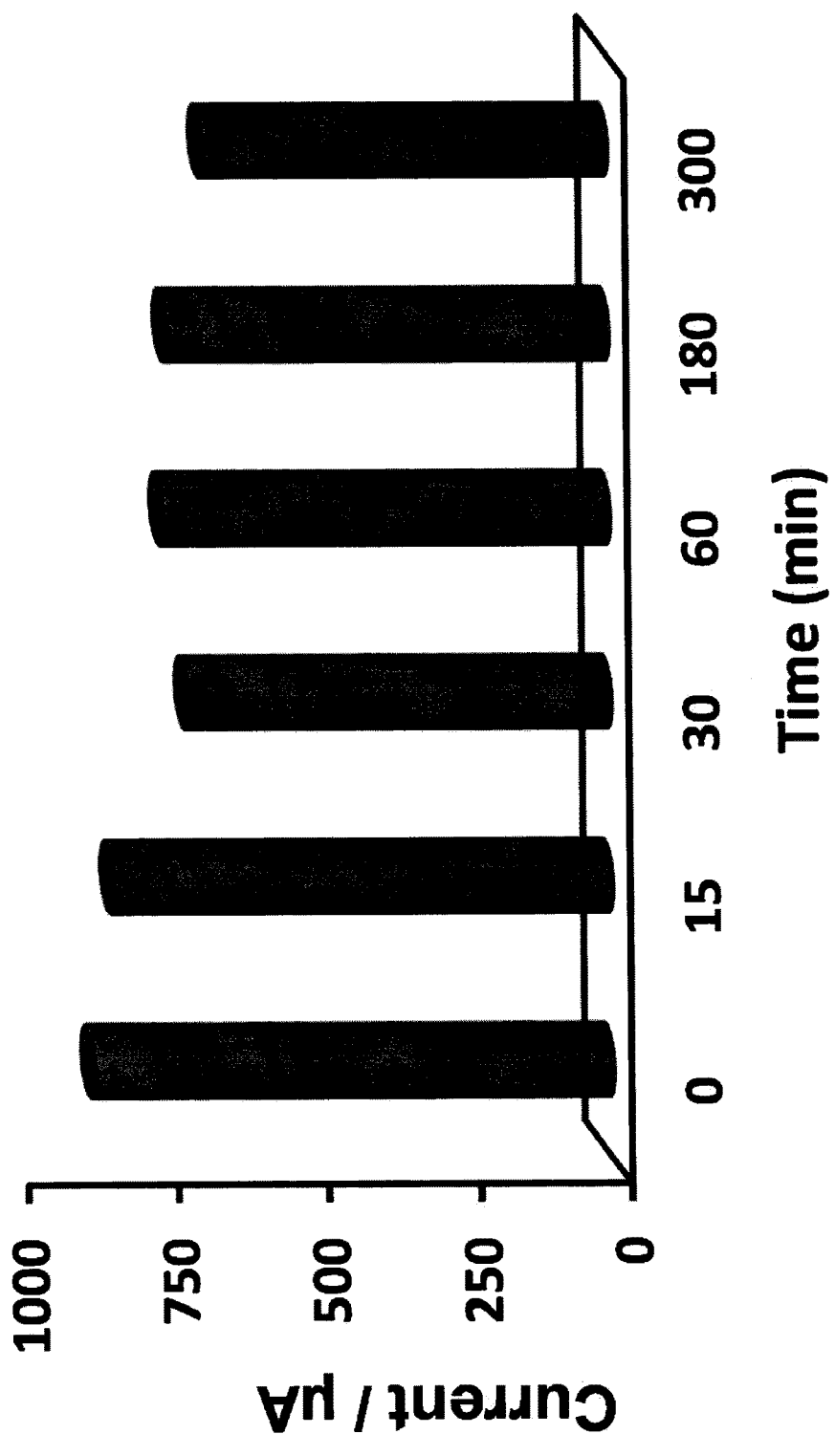
FIG. 13 is a graphical presentation of the relationship between the oxidation current peak height of the electropolymerized phenol determined by square wave voltammetry and the time of the storage of the GPE in a phosphate buffered saline (pH 7.2) following the contacting of the charged GPE with a phosphate buffered saline containing 50 µM phenol to electropolymerize the phenol on the charged surface of the GPE in open circuit fashion and prior to the square wave voltammetry according to Example 7.

Determination of the Stability of the Electropolymerized Phenol Formed on the Charged Surface of the GPE To determine the stability of the electropolymerized phenol formed on the charged surface of the GPE, following the charging of the GPE and the subsequent contacting of the charged GPE with a phosphate buffered saline containing 50 µM phenol to electropolymerize the phenol on the charged surface in open circuit fashion, the resulting GPE with the electropolymerized phenol formed on the charged surface was stored in a phosphate buffered saline (pH 7.2) for different times, i.e. 0 min, 15 min, 30 min, 60 min, 180 min, or 300 min prior to the SWV to determine the oxidation current peak heights at the oxidation peak potential of the electropolymerized phenol. Referring to FIG. 13, the oxidation current peak height at the oxidation peak potential of the electropolymerized phenol with the GPE having the electropolymerized phenol formed on the charged surface and stored in the phosphate buffered saline (pH 7.2) for 300 min, the longest time tested, prior to the SWV was reduced 22% as compared to that with the control GPE having the electropolymerized phenol formed on the charged surface but not stored (i.e. 0 min storage) in the phosphate buffered saline (pH 7.2) prior to the SWV, indicating that the electropolymerized phenol formed on the charged surface of the GPE is sufficiently stable for a reliable electrochemical determination of a phenol concentration by the SWV.

Example 8

Characterization of the Charged Graphite Pencil Electrode (GPE)

Figure 14:
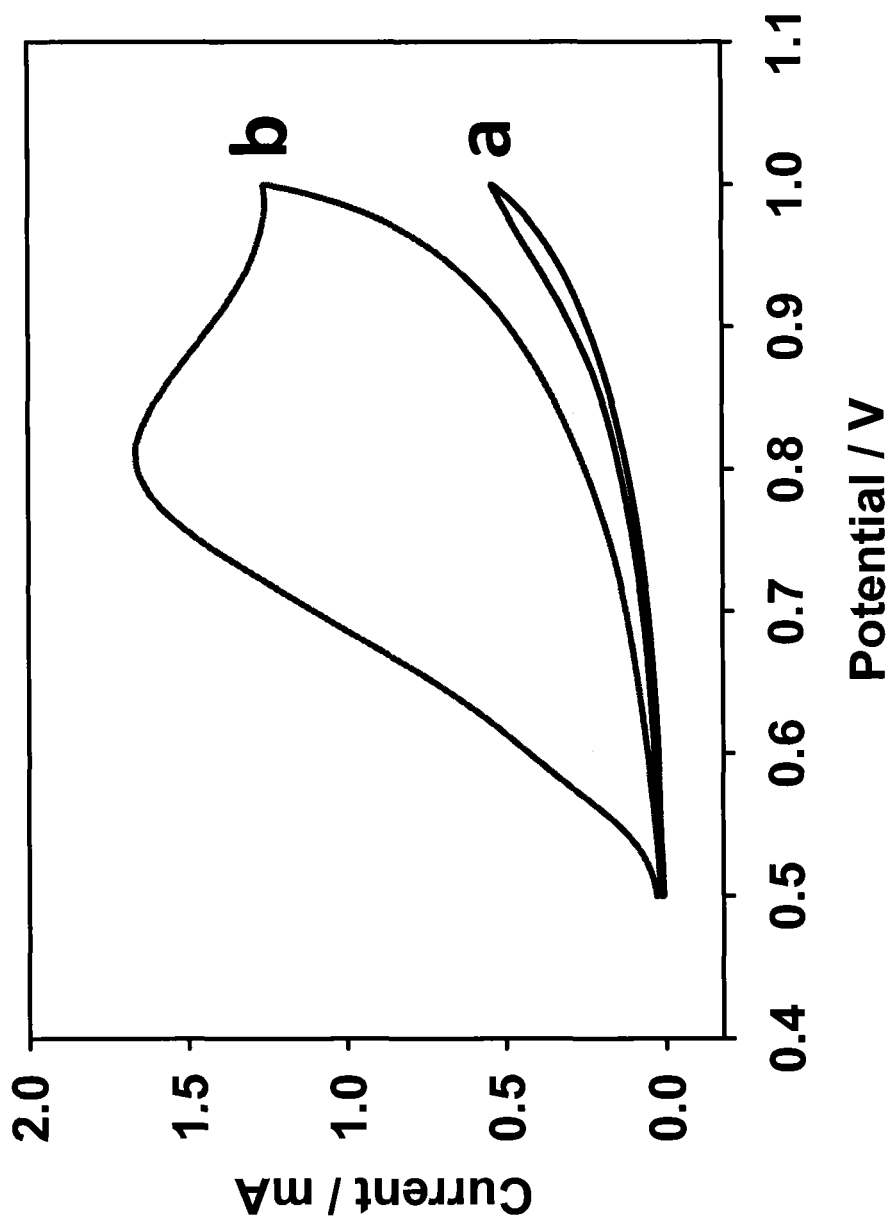
FIG. 14 is a graphical presentation of the cyclic voltammograms of the uncharged GPE represented by line (a), and the charged GPE represented by line (b), in 6 M NaOH with the scan rate of 2 mV/s according to Example 8.

FIG. 14 shows a comparison in the cyclic voltammetric behavior in a 6 M NaOH solution at a slow scan rate of 2 mV/s between the uncharged GPE surface represented by line (a) and the charged GPE surface represented by line (b). The charging of the GPE had been performed in 0.1 M NaOH as the charging solution. The specific capacitance for both surfaces calculated according to the equation $C=Q/\Delta E \cdot m$ (where Q is the voltammetric charge, m is the weight of the electrode and $\Delta E$ is the working potential window used for the CV, See T. Brousse, P. Taberna, O. Crosnier, R. Dugas, P. Guillemet, Y. Scudeller, Y. Zhou, F. Favier, D'B danger, P. Simon, J. Power Sources 2007, 173, 633-641, incorporated herein by reference in its entirety) and based on the integrated area under the corresponding CV curves were 187.51 F/g and 5734.81 F/g for the uncharged GPE and the charged GPE, respectively. The dramatic increase in the specific capacitance of the charged GPE surface may be responsible for its ability to carry out the electrochemical polymerization of phenol in open circuit fashion.

Figure 15:
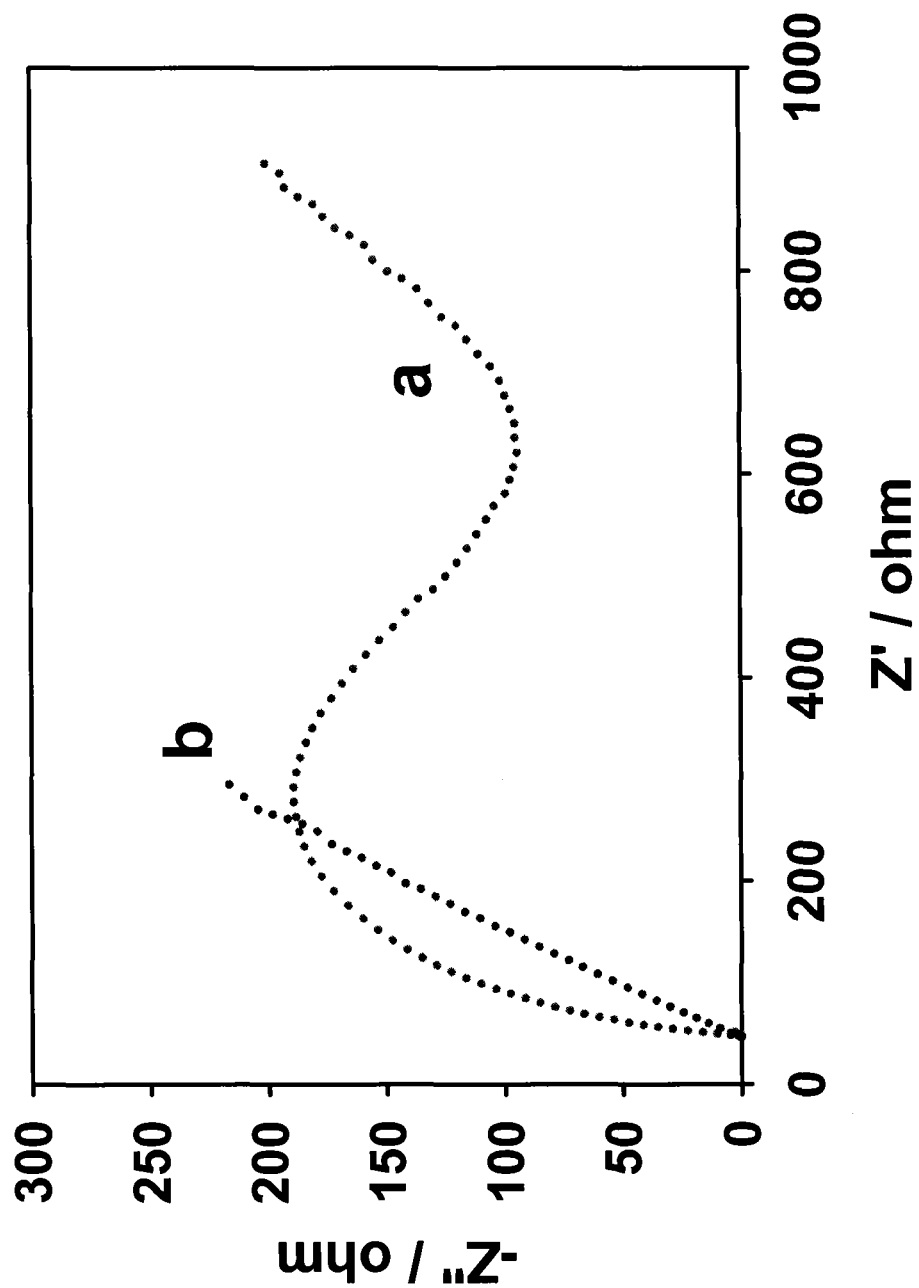
FIG. 15 a graphical presentation of the Nyquist plots of the uncharged GPE represented by line (a), and the charged GPE represented by line (b), in a 0.1 M KCl solution containing a mixture of 5 mM $K_4[Fe(CN)_6]$ and 5 mM $K_3[Fe(CN)_6]$ and in the frequency range of 100 kHz to 0.01 Hz according to Example 8.

Moreover, FIG. 15 shows the Nyquist plots of the uncharged GPE represented by line (a) and the charged GPE represented by line (b) in a 0.1 M KCl solution containing a mixture of 5 mM $K_4[Fe(CN)_6]$ and 5 mM $K_3[Fe(CN)_6]$ with a frequency range of 100 kHz to 0.01 Hz. The plot obtained with the uncharged GPE is composed of a semicircle and a straight line, whereas only a straight line was obtained with the charged GPE. Since the semicircle at a higher frequency region is attributed to the charge transfer process at the electrode/electrolyte interface, the straight line at a lower frequency region is ascribed to the diffusion process in solid (See A. Yuan, Q. Zhang, Electrochem. Comm. 2006, 8, 1173-1178, incorporated herein by reference in its entirety). Thus, the electrochemical reaction resistance at the charged GPE is comparatively much smaller. In addition, the straight line at a lower frequency region for the charged GPE has a greater slope than that for the uncharged GPE, suggesting that the former is more capacitive than the latter. These results are in agreement with the CV results shown in FIG. 14.

Figure 16:
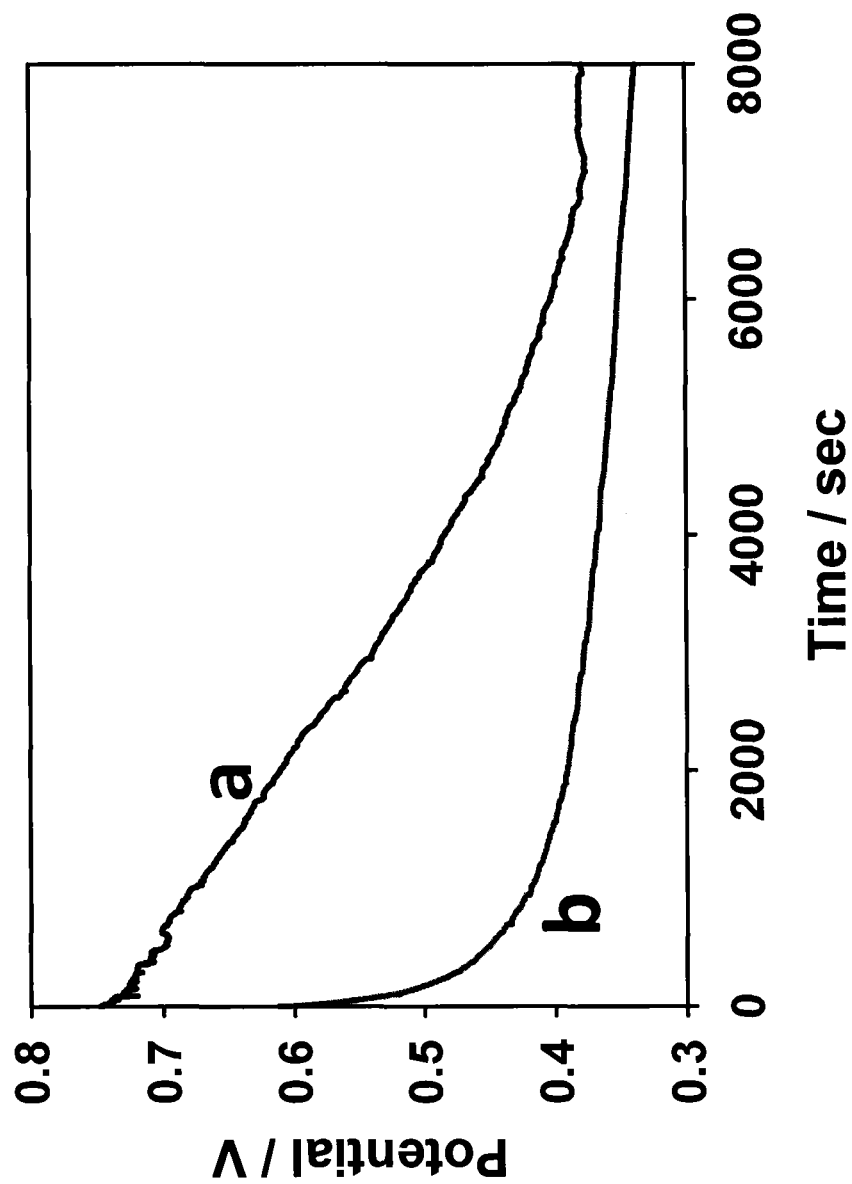
FIG. 16 is a graphical presentation of the open circuit potential of the charged GPE with time in 0.1 M PBS (pH 7.0) represented by line (a) or in 0.1 M PBS (pH 7.0) containing 100 µM phenol represented by line (b) according to Example 8.

Referring to FIG. 16, to confirm the pseudocapacitor performance of the charged graphite pencil electrode, a discharging experiment was performed for the charged GPE in the absence (represented by line (a)) or presence (represented by line (b)) of 100 μM phenol in 0.1 M PBS (pH 7.0). In the absence of phenol, the electrode discharge was linear and lasted for over 100 min, whereas in the presence of phenol the electrode got discharged quickly in a few minutes. This may be attributed to the charge consumption for the electropolymerization of phenol.

Example 9

Determination of Phenol Concentrations in Water Samples and Determination of Interference with Detecting Phenol Using the GPE System and SWV The possibility of detecting phenol in actual samples by the disclosed method using the GPE system and SWV was investigated. Phenol in actual water samples is typically at a concentration lower than the detection limit of the disclosed method, and therefore is undetectable. For this reason, 0.5 μM phenol was added to the water samples. A comparison between the added phenol concentration and the phenol concentrations detected by the GPE system and SWV indicated the phenol recovery rates of 99.25%, 107.07%, and 110.93% in drinking water collected from the filtration plant at the university, tap water, and commercial drinking water, respectively.

Figure 17:
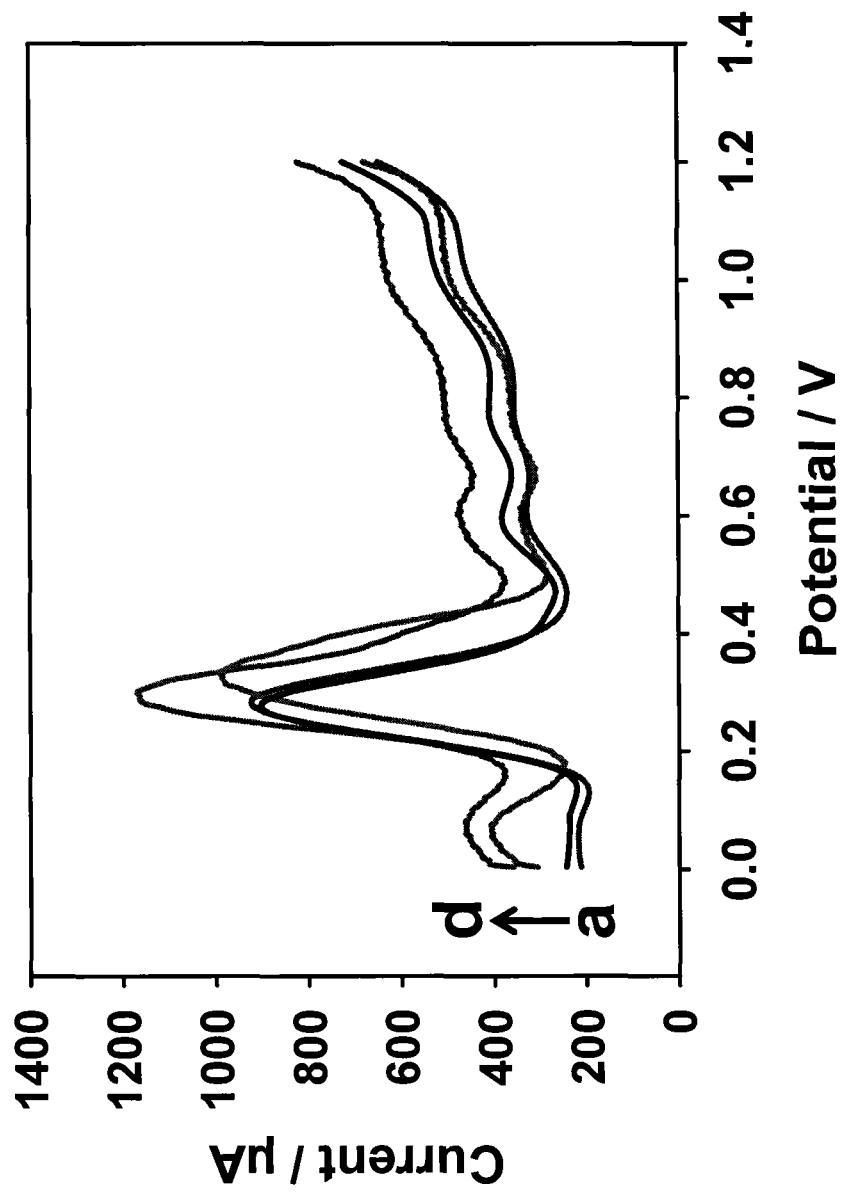
FIG. 17 is a graphical presentation of the square wave voltammograms with the GPE system that was charged and contacted with (a) 0.1 M PBS (pH 7.2) containing 0.5 µM phenol; (b) 0.1 M PBS (pH 7.2) containing 0.5 µM phenol and 0.5 µM each of $Co^{2+}$, $Cu^{2+}$, $Ca^{2+}$, $K^+$ and $Na^+$; (c) 0.1 M PBS (pH 7.2) containing 0.5 µM phenol and 0.5 µM 4-bromophenol; or (d) 0.1 M PBS (pH 7.2) containing 0.5 µM phenol and 0.5 µM 2,4-dichlorophenol to electropolymerize the phenol on the charged surface of GPE in open circuit fashion for 120 seconds prior to the square wave voltammetry in 0.1 M PBS (pH 7.0) as the SWV medium according to Example 9.
Figure 18:
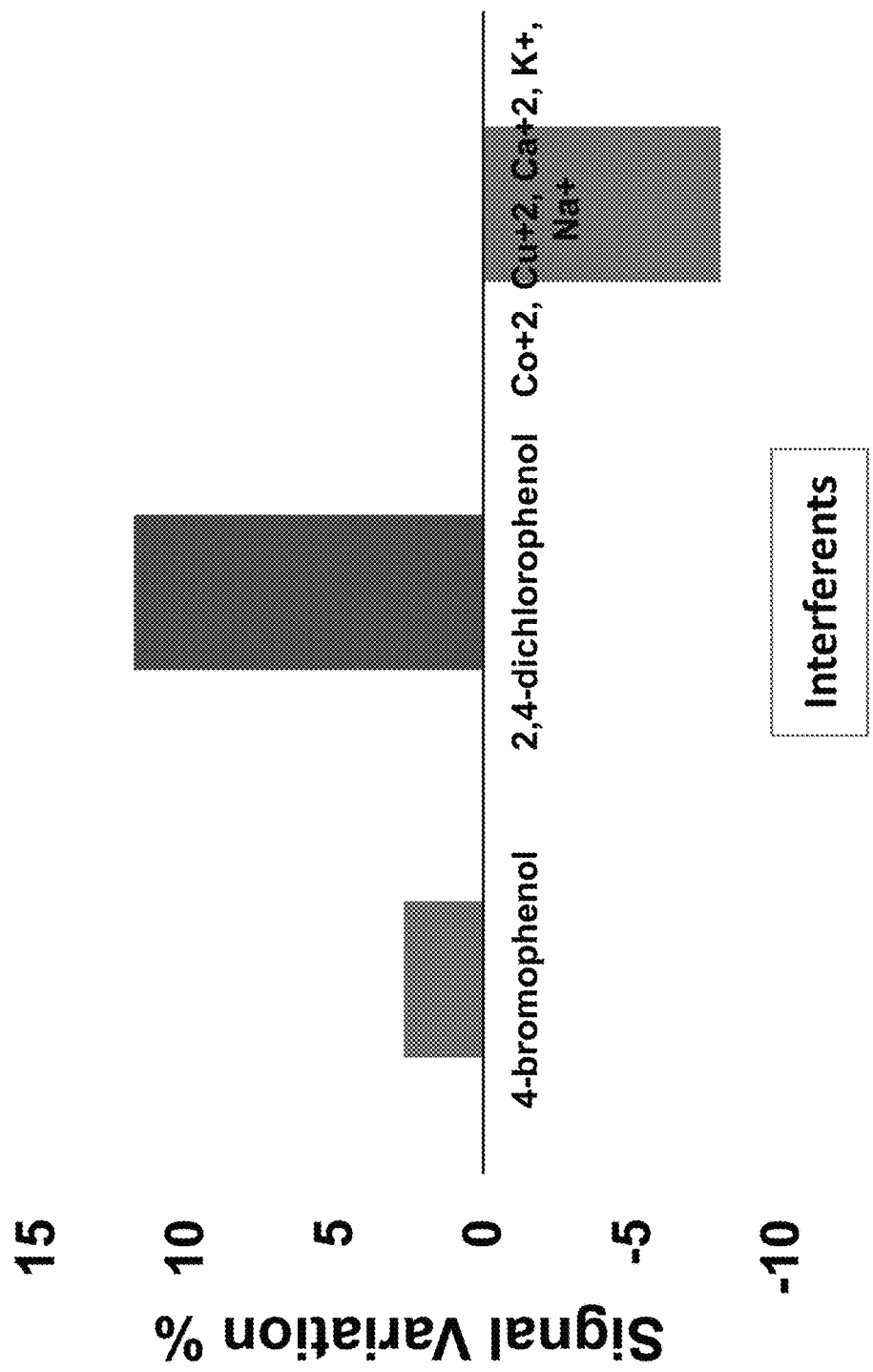
FIG. 18 is a graphical presentation of the variations in the oxidation peak current of the electropolymerized phenol between the 0.1 M PBS (pH 7.2) containing 0.5 µM phenol together with the indicated interferents and the 0.1 M PBS (pH 7.2) containing 0.5 µM phenol only derived from the square wave voltammograms of FIG. 17 according to Example 9.

Interference from metal cations and halogen derivatives of phenol with the sensitivity of phenol detection using the GPE system and SWV was examined by studying the effects of the above potential interferents on the oxidation peak current of the electropolymerized phenol. Referring to FIG. 17 and FIG. 18, an addition of 0.5 μM 4-bromopheonl, 0.5 μM 2,4-dichlorophenol, or a mixture of metal cations of $Co^{2+}$, $Cu^{2+}$, $Ca^{2+}$, $Na^+$, and $K^+$ at 0.5 μM each to a PBS containing 0.5 μM phenol introduced variations in the oxidation peak current of the electropolymerized phenol by +2.65%, +11.74%, and −7.96%, respectively, as compared to the oxidation peak current of the electropolymerized phenol formed from the control PBS containing 0.5 μM phenol only without the interferents. These experimental results indicate the good phenol detection sensitivity and selectivity, and stability of the electropolymerized phenol formed on the charged GPE.

The invention claimed is:

1. A method of determining a concentration of phenol and/or a phenol derivative in a first solution containing the phenol and/or the phenol derivative, the method comprising:
   (a) subjecting a graphite pencil electrode system to cyclic voltammetry in a second solution, wherein the graphite pencil electrode system comprises a graphite pencil working electrode, a counter electrode, and a reference electrode, and wherein a surface of the graphite pencil working electrode is charged by the cyclic voltammetry to form a charged surface,
   (b) contacting the charged surface of the graphite pencil working electrode with the first solution for a sufficient period of time in open circuit fashion, and
   (c) determining the concentration of the phenol and/or the phenol derivative in the first solution by placing the graphite pencil working electrode, the counter electrode, and the reference electrode in a third solution which does not contain phenol and/or a phenol derivative and subjecting to square wave voltammetry.

2. The method of claim 1, wherein the first solution has a pH of about 3-14.

3. The method of claim 1, wherein the second solution comprises at least one phosphate dibasic salt or at least one metal hydroxide.

4. The method of claim 1, wherein the cyclic voltammetry has a potential range of 0.6-4 V.

5. The method of claim 1, wherein the cyclic voltammetry has 20-80 voltammetric cycles.

6. The method of claim 1, wherein the cyclic voltammetry has a scan rate of 50-200 mV/s.

7. The method of claim 1, wherein the sufficient period of time in (b) is about 50-150 seconds.

8. The method of claim 1, wherein the phenol derivative is at least one selected from the group consisting of an alkylphenol, a catechol, a trihydroxybenzene, a bisphenol, and a hydroxybiphenyl.

9. The method of claim 1, wherein a time interval between the end of the subjecting in (a) and the start of the contacting in (b) is no greater than 15 minutes.

10. The method of claim 1, wherein the square wave voltammetry comprises:
 (a) applying a pulsed potential to the graphite pencil working electrode while sweeping the potential of the graphite pencil working electrode from a potential that is less than an oxidation peak potential in the third solution positively to a potential that is at least the oxidation peak potential in the third solution, and
 (b) recording the amount of a forward pulse current and a reverse pulse current during each square wave cycle.

11. The method of claim 10, wherein the third solution has a pH of 2-10.

12. The method of claim 10, wherein the oxidation peak potential ranges from about 0.0 V to about 1.0 V.

13. The method of claim 10, wherein the amplitude of the pulsed potential is about 0.02-0.10 V.

14. The method of claim 10, wherein a voltage step of the pulsed potential is about 3-5 mV.

15. The method of claim 10, wherein a frequency of the pulsed potential is about 10-100 Hz.

16. The method of claim 10, wherein the first solution has a lowest phenol concentration of about 3-60 nM.

17. The method of claim 10, wherein the square wave voltammetry further comprises plotting the difference in current between the forward pulse current and the reverse pulse current during each square wave cycle, the difference in current represented by i, against the applied potential of the graphite pencil working electrode to obtain a square wave voltammogram, and measuring the magnitudes of peak changes in i in the square wave voltammogram.

18. The method of claim 17, wherein the magnitude of the peak change in i occurring at the oxidation peak potential in the square wave voltammogram linearly correlates with the concentration of the phenol in the first solution ranging from about 0.05 µM to 5 µM.

19. The method of claim 18, wherein the linear correlation between the magnitude of the peak change in i occurring at the oxidation peak potential in the square wave voltammogram and the concentration of the phenol in the first solution is defined by a linear equation, and wherein a slope of the linear equation is at least 250 $\mu A\ \mu M^{-1}$.

20. The method of claim 1, wherein the second solution comprises NaOH at a concentration of 0.05-2 M.

* * * * *